United States Patent [19]
Doub et al.

[11] 4,053,470
[45] Oct. 11, 1977

[54] SUBSTITUTED-1,2-DIHYDRO-2-OXONICOTINYL-CEPHALOSPORINS

[75] Inventors: Leonard Doub; James S. Kaltenbronn; Dieter Schweiss, all of Ann Arbor, Mich.

[73] Assignee: Parke, Davis & Company, Detroit, Mich.

[21] Appl. No.: 650,098

[22] Filed: Jan. 19, 1976

Related U.S. Application Data

[60] Division of Ser. No. 534,031, Dec. 23, 1974, Pat. No. 3,954,734, which is a continuation-in-part of Ser. No. 434,763, Jan. 21, 1974, abandoned.

[51] Int. Cl.$^2$ .............. C07D 501/20; D61K 31/545; C07D 499/44
[52] U.S. Cl. .............................. 544/25; 424/246; 260/239.1; 544/27; 544/28
[58] Field of Search .................... 260/243 C

[56] References Cited
U.S. PATENT DOCUMENTS 3,948,903   4/1976   Doub et al. .............. 260/243 C
3,954,734   5/1976   Doub et al. .............. 260/243 C

*Primary Examiner*—Nicholas S. Rizzo
*Attorney, Agent, or Firm*—Stephen Raines; George M. Richards; David B. Ehrlinger

[57] ABSTRACT

Novel organic amide compounds which are N-[6-[(substituted amino)phenyl]-1 2-dihydro-2-oxonicotinyl]-penicillin and cephalosporin type compounds having broad spectrum antibacterial utility are provided by (a) reacting the free amino acid of the appropriate penicillin or cephalosporin or the acid salt or silylated derivative thereof with a reactive derivative of the corresponding N-6-[(substituted amino)phenyl]-1,2-dihydro-2-oxonicotinic acid or (b) reacting the free amino acid 6-amino-penicillanic acid, 7-aminocephalosporanic acid, 7-amino-3-methylceph-3-em-4-carboxylic acid or a related compound or the acid salt or silylated derivative thereof with a reactive derivative of the corresponding D-N-[6-[(substituted amino)phenyl]-1,2-dihydro-2-oxonicotinyl]-2-substituted glycine. Pharmaceutical compositions containing said compounds and methods for treating infections using said compositions are also disclosed.

4 Claims, No Drawings

SUBSTITUTED-1,2-DIHYDRO-2-OXONICOTINYL-CEPHALOSPORINS

This application is a divisional application of copending application, Ser. No. 534,031, filed Dec. 23, 1974, now U.S. Pat. No. 3,954,734, which is a continuation-in-part of copending application, Ser. No. 434,763, filed Jan. 21, 1974, now abandoned.

SUMMARY AND DETAILED DESCRIPTION

The present invention relates to novel chemical compounds that are useful as pharmacological agents and to methods for their production. More particularly, the invention relates to novel organic amide compounds having the formulae and pharmaceutically-acceptable salts thereof; wherein R is hydrogen or methyl; $R_1$ and $R_2$ are hydrogen, straight or branched lower alkyl groups of from one to six carbon atoms or $R_1R_2N$ taken together is nitro, 4-$R_5$-1-piperazinyl, 4-methyl-1-homopiperazinyl, 1-pyrrolidinyl, morpholinyl, 1-piperidinyl, 4-(1-pyrrolidinyl)-piperidinyl or 4-(1-piperidinyl)piperidinyl, wherein $R_5$ is a lower alkyl group of from one to six carbon atoms, cyclohexyl, benzyl, phenyl and halopenyl wherein halo represents chloro, fluoro, bromo, or iodo, $R_3$ is phenyl, p-hydroxyphenyl, 2-thienyl and cyclohexa-1,4-dien-1-yl and $R_4$ is hydrogen, acetoxy, (5-methyl-1,3,4-thiadiazol-2-yl)thio, (2-pyrimidinyl)thio and 1-pyridyl with the proviso that when $R_4$ is 1-pyridyl, the $CO_2H$ is $—CO_2^-$; X is hydrogen, chlorine or bromine and Y is hydrogen or bromine.

The preferred compounds being those wherein R is hydrogen; $R_1$ and $R_2$ are ethyl or $R_1R_2N$ taken together is 4-$R_5$-1-piperazino wherein $R_5$ is a straight or branched lower alkyl group of from one to six carbon atoms or benzyl and $R_3$ is phenyl or p-hydroxyphenyl. The most preferred compounds are those wherein the $R_1R_2N$ group is M-diethylamino and p-(4-methyl-1-piperazino).

In accordance with the invention the foregoing amide compounds having the formula

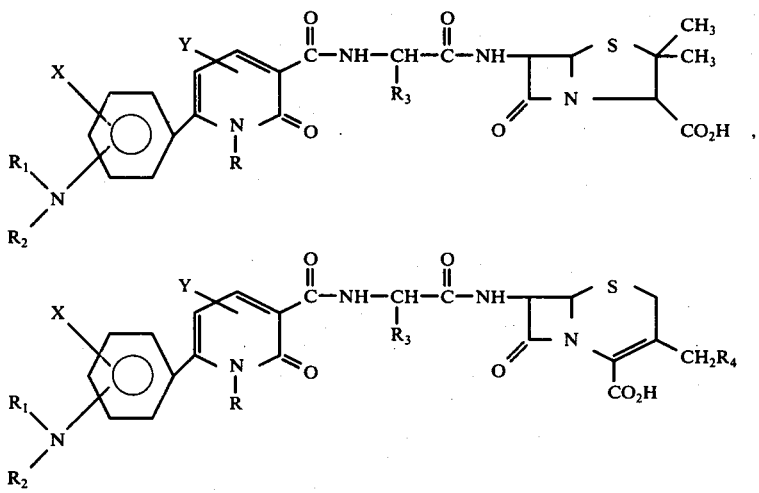

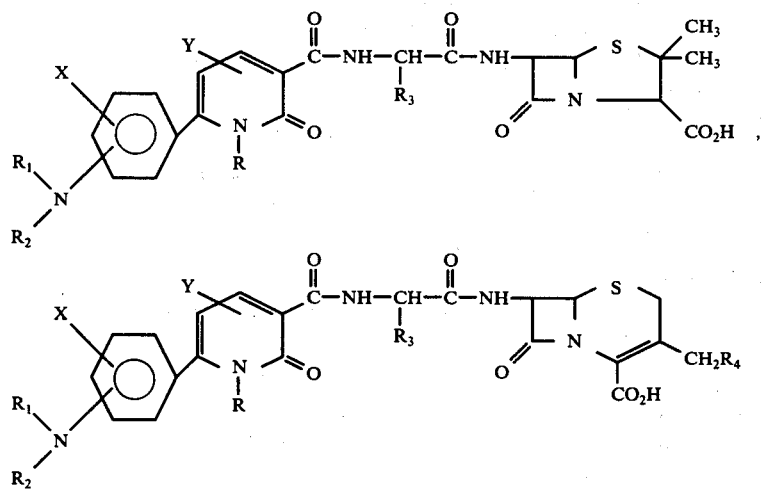

and pharmaceutically acceptable salts thereof wherein R, $R_1$, $R_2$, $R_1R_2N$, $R_3$, $R_4$, X and Y are as previously defined are produced by reacting a compound of the formulae

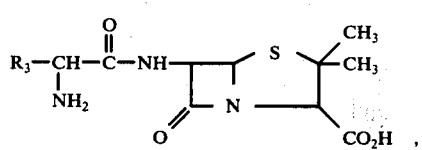

-continued

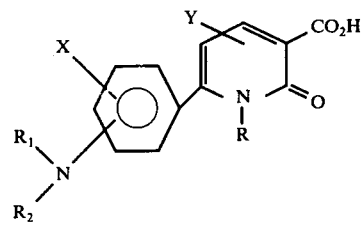

or the acid salt or silylated derivative (preferrably the disilylated) thereof wherein $R_3$ and $R_4$ are as previously defined, with a 1,2-dihydro-2-oxonicotinic acid compound having the formula

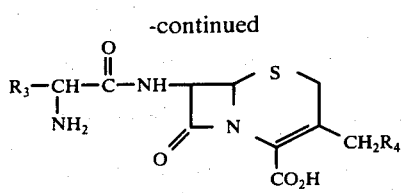

or its acid addition salts or a reactive derivative thereof; where R, $R_1$, $R_2$, X and Y all have the aforementioned significance. For the reaction the 6-[(substituted amino)-phenyl]-1,2-dihydro-2-oxonicotinic acid can be employed in activated form by using a carbodiimide, such as N,N'-dicyclohexylcarbodiimide (in a manner known to those skilled in the art). Some examples of reactive derivatives of the 6-[(substituted amino)phenyl]-1,2-dihydro-2-oxonicotinic acid compound suitable for the reaction are the acid halides (especially the acid chloride), the imidazolide, mixed anhydrides (especially those formed from an alkyl chloroformate such as ethyl chloroformate and isobutyl chloroformate), and activated esters such as the pentachlorophenyl ester.

The reactants are normally employed in approximate equimolar quantities, although an excess of either (oxonicotinic acid compound or amino acid compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the penicillin and cephalosporin type compounds in the free acid or salt form, aqueous solutions may be used for acylation with an acid halide or mixed anhydride under normal Schotten-Baumann conditions. The duration and temperature of the reaction are not critical. Temperatures in the range from $-30°$ to $+30°$ C are commonly used for reaction times ranging from a few hours up to a day or more. The product may be isolated in any suitable way as the free acid or as a salt by appropriate adjustment of the pH.

The 6-[(substituted amino)phenyl]-1,2-dihydro-2-oxonicotinic acid compounds and their reactive derivatives which are required as starting materials in the foregoing process can be prepared according to any of a variety of methods as illustrated in greater detail hereinafter.

A compound of the formula

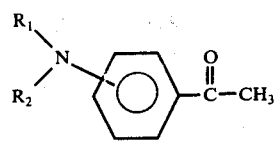

is prepared by alkylating a compound of the formula

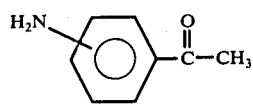

with an alkylating agent, such as an alkyl iodide or dialkyl sulfate, or reacting a compound of the formula

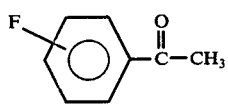

wherein the fluorine is in the ortho or para position, with a compound of the formula

In addition, the fluoro atom may be activated for easier removal, especially if it is in the meta position by the presence of a nitro group.

Thus, a compound of the formula

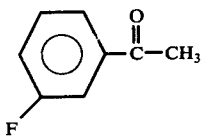

is nitrated in fuming nitric acid to give

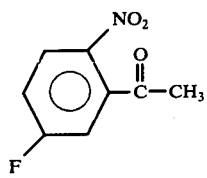

which in turn is reacted with a compound of the formula

yielding a compound of the formula

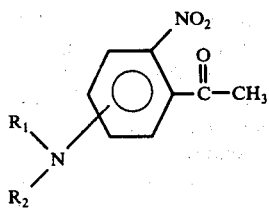

The nitro group is removed by catalytically reducing the nitro group to an amino group, then treating a salt of the resultant amine with sodium nitrite followed by water.

A method for preparing halo substituted starting materials relies on reacting a compound of the formula

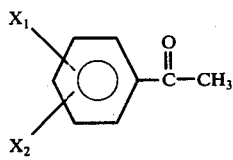

wherein $X_1$ and $X_2$ are either bromine or chlorine, with a compound of the formula $R_1R_2NH$ to give

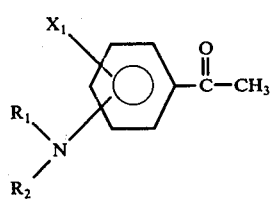

The compound of the formula

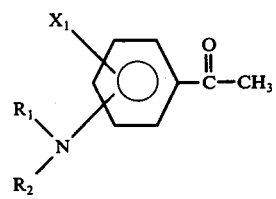

is reacted with a lower alkyl formate, such as ethyl formate, in the presence of a strong base, such as sodium methoxide or sodium hydride, to give the sodium salt of the following dicarbonyl compound

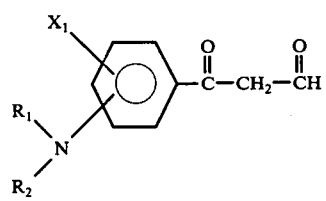

The above compounds in turn are reacted with 2-cyanoacetamide or N-methyl-2-cyanoacetamide in the presence of piperidine acetate to give the following nitrile

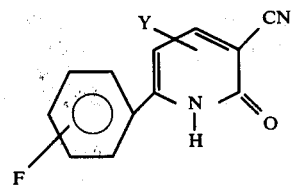

wherein $X_3$ is hydrogen, chlorine or bromine.

The above nitrile wherein $X_3$ is hydrogen and Y is hydrogen or bromine may also be prepared by reacting a compound of the formula

wherein the fluorine is in the ortho or para position, with a compound of the formula

R₁\
 NH
R₂/

The nitriles prepared by the above procedures are converted to the desired 6-[(substituted amino)phenyl]-2-dihydro-2-oxonicotinic acid by conversion of the cyano group to a carboxyl group utilizing an aqueous solution of a strong base.

The 6-[(substituted amino)phenyl]-1,2-dihydro-2-oxonicotinic acid may be converted to its acid chloride utilizing thionyl chloride, its mixed anhydride utilizing ethyl chloroformate, its pentachlorophenyl ester by esterification with pentachlorophenol and its imidazolide by reacting the acid with 1,1'-carbonyldiimidazole.

The silylated amino acid starting materials can be prepared by reacting an amino acid of the formulae

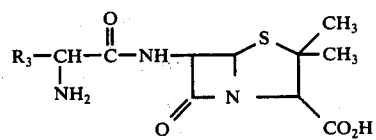

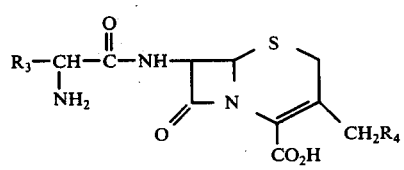

or a salt thereof wherein $R_3$ and $R_4$ are as previously defined in anhydrous form with either one or two equivalents of a tri(lower alkyl) silyl chloride in the presence of triethylamine. The preferred silylating agents are trimethylsilyl chloride and dimethyl dichlorosilane. When two equivalents of the silylating agent are used, both the amino and the carboxyl group become silylated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formulae

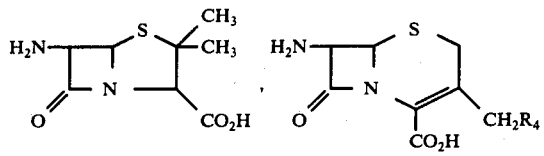

or the corresponding acid salt or silylated derivative thereof wherein $R_4$ is a previously defined with a D-N-[6-[(substituted amino)phenyl]-1,2-dihydro-2-oxonicotinyl]-2-phenylglycine having the formula

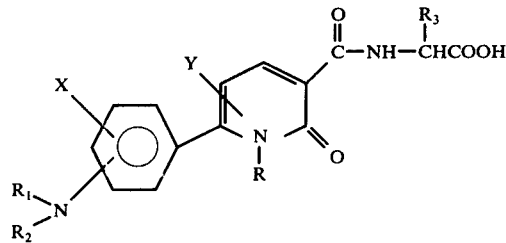

or its acid addition salts or a reactive derivative thereof, where R, $R_1$, $R_2$, $R_3$, X and Y have the aforementioned significance.

Some examples of reactive derivatives of the D-N-(1,2-dihydro-2-oxonicotinyl)-2-substituted glycine compounds suitable for the reaction are the acid halides, the imidazolide, mixed anhydrides (especially those formed from an alkyl chloroformate such as ethyl chloroformate and isobutyl chloroformate), and activated esters such as the pentachlorophenyl ester. Since racemization is more likely with the acid halide, the other forms are generally preferred. The reactants are normally employed in approximate equimolar quantities, although an excess of either (oxonicotinic acid compound or amino acid compound) can be used if desired. The reaction can be carried out in any of a number of unreactive solvents. When using the silylated derivative for the reaction the solvent should be anhydrous and may include tertiary amindes (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 6-aminopenicillanic acid and 7-amino-3-$R_4CH_2$ceph-3-em-4 carboxylic acid may be reacted with an acid chloride or mixed anhydride in the free acid or salt form using aqueous solution under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The N-[6-[substituted amino)phenyl]-1,2-dihydro-2-oxonicotinyl]-2-substituted glycines and their reactive derivatives which are required as starting materials in the foregoing process can be prepared by methods illustrated in greater detail hereinafter.

The desired N-[6-[(substituted amino)phenyl]-1,2-dihydro-2-oxonicotinyl)-2-substituted gylcine may be prepared by reacting the corresponding 6-[(substituted amino)-phenyl]-1,2-dihydro-2-oxonicotinyl chloride with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formulae

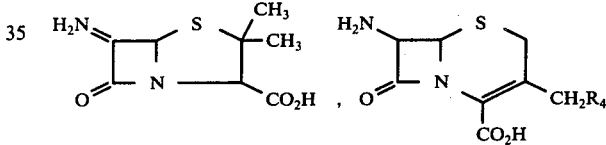

with a hexaalkyldisilazane. The preferred silylating agent is hexamethyldisilazane. Only the carboxyl group is silylated under the conditions used (e.g., 2-hour reflux in dichloromethane). After acylation, the silyl group is easily removed by treatment with water.

Compounds of this invention have the formulae

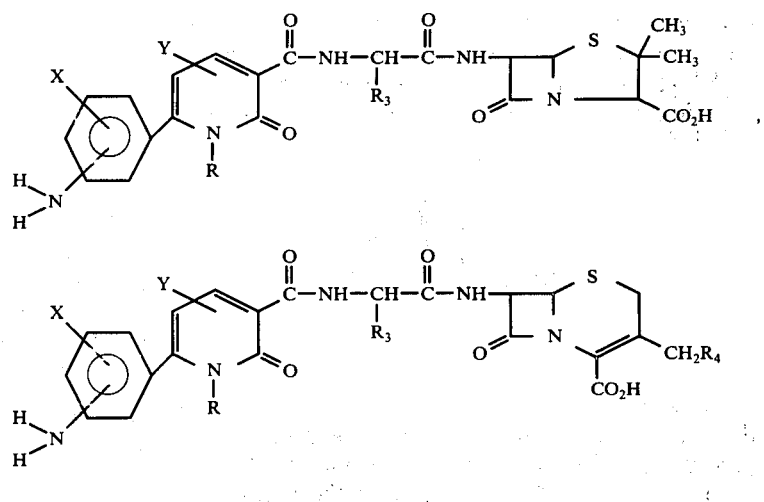

and pharmaceutically-acceptable salts thereof, where R, $R_3$, $R_4$, X and Y are as previously defined may also be prepared by reducing a compound of the formulae

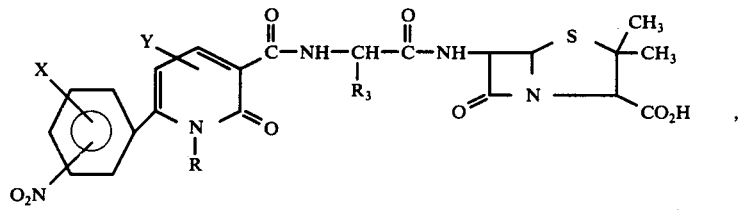

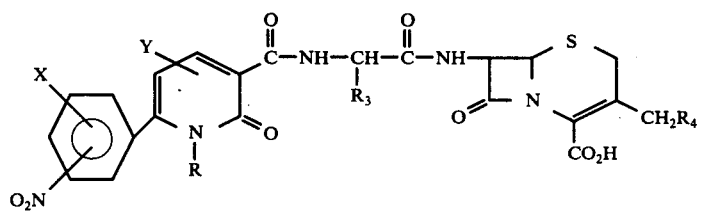

or pharmaceutically-acceptable salts thereof and isolating the product or adjusting the pH and isolating the product.

While chemical reduction procedures may be employed, a catalytic procedure is preferred. Of the numerous noble metal catalysts that may be used, palladium on a barium sulfate (about twenty percent palladium) support is preferred. The ratio of catalyst to nitro compound is not critical and may vary from about one percent to about fifty percent. Standard hydrogenation solvents may be employed such as tetrahydrofuran, water, ethanol or mixtures thereof. The reaction is generally conducted at temperatures of from about 0° to 45°, preferrably at room temperature and at pressures of from about atmospheric pressure to pressure to over 100 pounds per square inch, preferably 50 pounds per square inch. The reaction is carried out until hydrogen uptake is complete.

The nitro containing starting materials are prepared by the earlier described methods.

Lastly, compounds of the formula

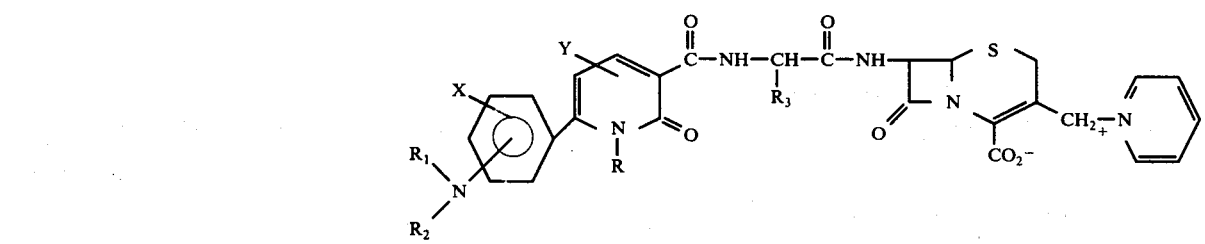

may be prepared by reacting a compound of the formula

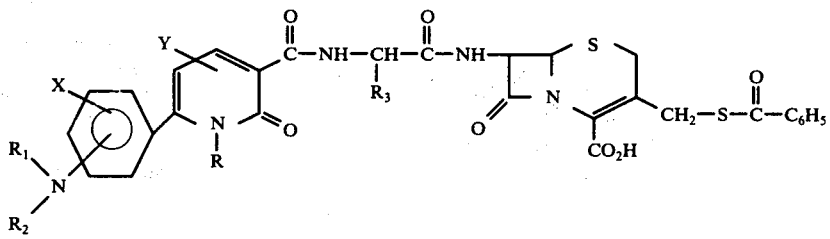

wherein R, $R_1$, $R_2$, $R_1R_2N$, $R_3$, $R_5$, X and Y are as previously defined, with pyridine in the presence of mercuric perchlorate. The ratio of reactants is not critical although generally an excess of pyridine is used in relation to cephalosporin compound. The mercuric perchlorate may also be used in slight excess when compared to the quantity of cephalosporin compound employed; however, the excess of this material is decomposed by use of an agent such as hydrogen sulfide prior to isolating the product.

A polar solvent which is inert to the mercuric perchlorate, such as water, is generally employed. Temperatures of from room temperature to 80° and times of from 15 minutes to 24 hours are generally used with a shorter time period being used when carrying out the reaction at a higher temperature.

The necessary starting material of the formula

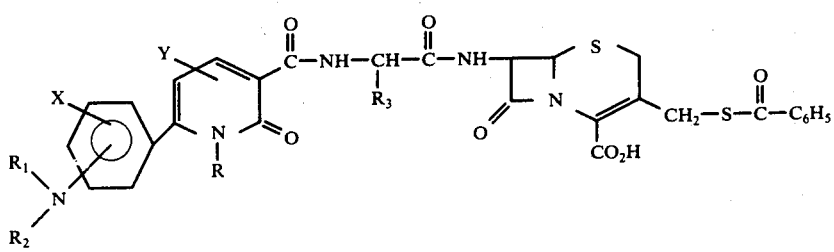

is prepared by reacting the trimethylsilyl derivative of a compound of the formula

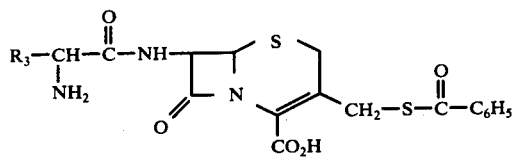

with a compound of the formula

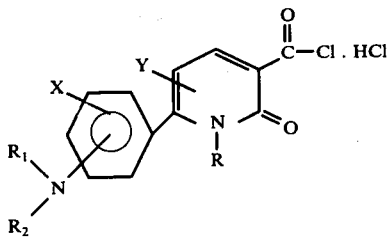

wherein R, $R_1$, $R_2$, $R_1R_2N$, X and Y are as previously defined, in the presence of trimethylamine. The reaction is generally conducted in N,N-dimethylacetamide for a period of about 1 hour at room temperature.

The free acids of the invention form carboxylate salts with any of a variety of inorganic and organic bases. Pharmaceutically-acceptable carboxylate salts are formed by reacting the free acids with such bases as sodium hydroxide, sodium carbonate, sodium bicarbonate, sodium 2-ethylhexanoate, potassium hydroxide, potassium carbonate, potassium 2-ethylhexanoate, calcium hydroxide, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention. In addition, the compounds of the invention can exist in the form of an acid-addition salt. Pharmaceutically-acceptable salts are formed by reaction of the free base or a carboxylate salt with any of a number of inorganic and organic acids, including hydrochloric, sulfuric, nitric, phosphoric, acetic, benzoic, citric, maleic, malic, tartaric, succinic, gluconic, ascorbic, sulfamic, pamoic, methanesulfonic, benzenesulfonic, and related acids.

The compounds of the invention can exist in anhydrous form, as well as in solvated, including hydrated, forms. In general, the hydrated forms and the solvated forms with pharmaceutically-acceptable solvents are equivalent to the anhydrous or unsolvated forms for the purposes of the invention.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for the following preferred compounds.

Thus, the compounds of this invention and their nontoxic pharmaceutically-acceptable salts are highly useful as broad spectrum antibiotics in mammals when administered in amounts ranging from about 5 mg. to about 100 mg. per kg. of body weight per day. A preferred dosage regimen for optimum results would be from about 10 mg. to about 50 mg. per kg. of body weight per day, and such dosage units are employed that a total of from about 700 mg. to about 3500 mg. of active ingredient for a subject of about 70 kg. body weight are administered in a 24 hour period.

While the compounds of this invention may be administered orally in the form of tablets, capsules, syrups, etc., (for treating infections of the alimentary tract) the preferred route of administration is parenterally for treating systemic infections.

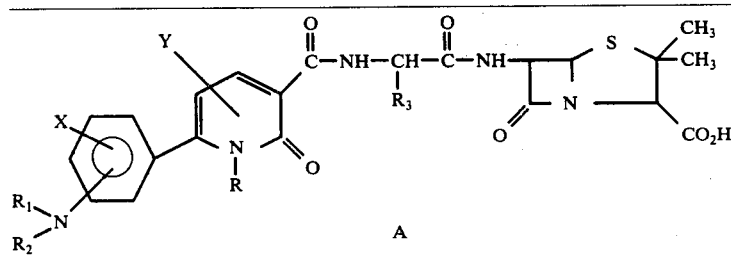

A

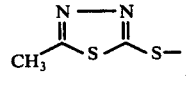

B

| $R_1\diagdown N$ $R_2\diagup$ | R | $R_3$ | $R_4$ | X | Y | Salt Form | General Formula | Pseudomonas aeruginosa γ/ml. | Enterobacter cloaca γ/ml. | Serratia marcescens γ/ml. | Klebsiella pneumoniae γ/ml. |
|---|---|---|---|---|---|---|---|---|---|---|---|
| p-(CH₃—N⌬N—) | H | —⟨phenyl⟩ | — | H | H | Na | A | 6.3 | 3.1 | 100 | 3.1 |
| p-(CH₃—N⌬N—) | H | HO—⟨phenyl⟩ | — | H | H | Na | A | 0.8 | 0.8 | 100 | 0.8 |
| p-(CH₃—N⌬N—) | H | ⟨thienyl⟩ | — | H | H | Na | A | 6.3 | 12.5 | 100 | 3.1 |
| m-(CH₃—N⌬N—) | H | C₆H₅ | — | H | H | Na | A | 3.1 | 3.1 | 25 | 0.8 |
| m-(CH₃—N⌬N—) | H | C₆H₅ | CH₃C(O)—O— | H | H | Na | B | 12.5 | 6.3 | — | — |
| m-[(CH₃)₂N—] | H | C₆H₅ | CH₃C(O)—O— | H | H | Na | B | 12.5 | 6.3 | 25 | 6.3 |
| m-[(C₂H₅)₂N—] | H | C₆H₅ | — | H | H | Na | A | 3.1 | 1.6 | 1.6 | 0.8 |
| m-[(CH₂H₅)₂N—] | H | C₆H₅ | CH₃C(O)—O— | H | H | Na | B | 12.5 | 1.6 | 12.5 | 0.8 |
| p-(CH₃—N⌬N—) | CH₃ | C₆H₅ | — | H | H | — | A | 6.3 | 6.3 | 50 | 3.1 |
| 4-(CH₃—N⌬N—) | H | C₆H₅ | — | 3-Cl | H | — | A | 3.1 | 3.1 | 12.5 | 0.4 |
| 4-(CH₃—N⌬N—) | H | C₆H₅ | — | 3-Br | Br | — | A | 6.3 | 50 | 100 | 12.5 |
| p-(CH₃—N⌬N—) | H | C₆H₅ | 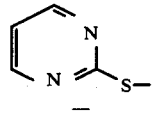 | H | H | Na | B | 12.5 | 12.5 | 200 | 12.5 |
| p-(CH₃—N⌬N—) | H | C₆H₅ | 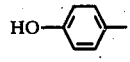 | H | H | Na | B | 25 | 25 | >200 | 12.5 |
| m-(H₂N—) | H | C₆H₅ | — | H | H | — | A | 6.3 | 3.1 | 25 | 3.1 |
| m-(H₂N—) | H | C₆H₅ | CH₃C(O)—O— | H | H | — | B | 12.5 | 12.5 | — | — |
| m-[(CH₃)₂N—)] | H | HO—⟨phenyl⟩ | — | H | H | Na | A | 12.5 | 12.5 | 25 | 6.3 |

-continued

Structure A:

$$\text{Y-[ring with X, R_1R_2N-]-}\overset{O}{\underset{}{C}}\text{-NH-CH(R_3)-}\overset{O}{\underset{}{C}}\text{-NH-[β-lactam]-S-C(CH}_3\text{)}_2\text{-CH(CO}_2\text{H)}$$

A

Structure B: analogous with =CH-CH$_2$R$_4$ and CO$_2$H

B

| R$_1$R$_2$N— | R | R$_3$ | R$_4$ | X | Y | Salt Form | General Formula | Pseudomonas aeruginosa γ/ml. | Enterobacter cloaca γ/ml. | Serratia marcescens γ/ml. | Klebsiella pneumoniae γ/ml. |
|---|---|---|---|---|---|---|---|---|---|---|---|
| m-(piperidin-N—) | H | C$_6$H$_5$ | — | H | H | — | A | 12.5 | 3.1 | 12.5 | 3.1 |
| p-(CH$_3$-N⟨⟩N—) | H | C$_6$H$_5$ | — | H | H | Na | A | 0.8 | 0.8 | 50 | 1.6 |
| p-(⟨N⟩N—) piperidinyl | H | C$_6$H$_5$ | — | H | H | Na | A | 6.3 | 6.3 | 50 | 6.3 |
| p-[(CH$_3$)$_2$N—] | H | C$_6$H$_5$ | — | H | H | Na | A | 6.3 | 6.3 | 25 | 3.1 |
| p-(C$_6$H$_5$-N⟨⟩N—) | H | C$_6$H$_5$ | — | H | H | Na | A | 3.1 | 3.1 | 50 | 3.1 |
| p-(C$_6$H$_5$-CH$_2$-N⟨⟩N—) | H | C$_6$H$_5$ | — | H | H | — | A | 6.3 | 0.4 | 3.1 | 0.8 |
| m-[(CH$_3$)$_2$N—] | H | C$_6$H$_5$ | — | H | H | Na | A | 6.3 | 3.1 | 6.3 | 3.1 |
| p-(C$_2$H$_5$-N⟨⟩N—) | H | C$_6$H$_5$ | — | H | H | — | A | 3.1 | 3.1 | 50 | 3.1 |
| p-(n-C$_3$H$_7$-N⟨⟩N—) | H | C$_6$H$_5$ | — | H | H | — | A | 3.1 | 3.1 | 50 | 3.1 |
| p-(CH$_3$-N⟨⟩N—) | H | C$_6$H$_5$ | CH$_3$C(O)-O— | H | H | Na | B | 12.5 | 6.3 | >200 | 6.3 |
| p-(O⟨⟩N—) morpholino | H | C$_6$H$_5$ | — | H | H | Na | A | 6.3 | 3.1 | 25 | 6.3 |

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg. to about 1000 mg. of active compound per vial. The vial may also contain other active ingredients, buffers, salts, etc. The sterile material in the vial is dissolved in water for injection at the time of use.

The invention is illustrated by the following examples.

EXAMPLE 1

Triethylamine, in the amount of 627 g., is added to a stirred suspension of 2500 g. of ampicillin trihydrate in 28.5 liters of dry acetonitrile which is cooled to 7°-8°. The mixture is stirred for 1.3 hours at 5° and the resulting precipitate of the triethylamine salt of ampicillin is collected by filtration, washed in turn with cold acetonitrile, with ether and with petroleum ether, then dried at reduced pressure.

Trimethylsilyl chloride, in an amount of 103 g., is added to a stirred suspension of 210 g. of the triethylamine salt of ampicillin in 1900 ml. of dichloromethane followed by the addition of 189 ml. of triethylamine. The mixture is stirred at 15° for 30 minutes, then 209 g. of 6-[p-(4-methyl-1-piperazinyl)phenyl]-1,2-dihydro-2-oxonicotin chloride hydrochloride is added. The mixture is stirred at room temperature for 16 hours, then diluted with 4 liters of ice water and acidified to a pH of 5.8 with hydrochloric acid. The precipitate of N-[6-[p-(4-methyl-1-piperazinyl)-phenyl]-1,2-dihydro-2-oxonicotinyl]ampicillin is collected by filtration and dried. This substituted ampicillin is dissolved in acetonitrile and the solution is treated with one equivalent of triethylamine. The resulting precipitate of the triethylamine salt is collected by filtration and dried. This triethylamine salt is dissolved in 1:1 tetrahydrofuran-acetonitrile and the solution is treated with one equivalent of a 50% solution of sodium 2-ethylhexanoate in 1-butanol. The resulting precipitate of the sodium salt is collected by filtration, washed with ether and dried; $[\alpha]_d^{25} + 188°$ (1.02% in 3:1 dimethylformamide-pyridine).

A 250 ml. solution of 0.2N aqueous sodium hydroxide is added carefully to a suspension of 64.5 g. of the substituted ampicillin in 250 ml. of acetone and the mixture stirred at room temperature for 30 minutes. The resulting solution is filtered and the filtrate poured with stirring into 6 liters of acetone. N-[6-[p-(4-Methyl-1-piperazinyl)phenyl-1,2-dihydro-2-oxonicotinyl]ampicillin in the form of its hemisodiuum salt (a 1:1 mixture or complex of the substituted ampicillin and its sodium salt) is collected by filtration, washed with acetone and with ether, then dried; $[\alpha]_d^{25} + 178°$ (1.02% in 3:1 dimethylformamide-pyridine).

A solution of 644.7 mg. of N-[6-[p-(4-methyl-1-piperazinyl)phenyl]-1,2-dihydro-2-oxonicotinyl]ampicillin in 10 ml. of dimethylacetamide is filtered and the filtrate treated with 0.25 ml. of a 4.8N solution of hydrogenchloride in isopropanol. Addition of ethyl acetate gives a yellow solid which is collected, washed with ethylacetate and dried. The yellow solid which is obtained in a yield of 668 mg. is shown by analysis to be N-[6-[p-(4-methyl-1-piperazinyl)phenyl]-1,2-dihydro-2-oxonicotinyl]ampicillin monohydrochloride $[\alpha]_d^{25} + 139°$ (0.965% in MeOH).

EXAMPLE 2

A suspension of 2.0 g of sodium ampicillin in 59 ml. of N,N-dimethylacetamide is cooled and treated with 1.45 ml. of trimethylsilyl chloride and 0.8 ml. of triethylamine, and the mixture is stirred at room temperature for 1 hour. The resulting suspension is cooled and treated with 1.6 ml. of triethylamine followed by 2.5 g. of 6-[p-(4-piperidinopiperidino)phenyl]-1,2-dihydro-2-oxonicotinyl chloride hydrochloride. The mixture is stirred at room temperature for 16 hours, then diluted with 200 ml. of water and acidified to pH 5.4 with hydrochloric acid. The precipitate of N-[6-[p-(4-piperidinopiperidino)phenyl]-1,2-dihydro-2-oxonicotinyl]ampicillin is collected by centrifugation. This substituted ampicillin is dissolved in 25 ml. of N,N-dimethylacetamide and the solution is treated with 1.5 ml. of a 50% solution of sodium 2-ethylhexanoate in 1-butanol. The solution thus obtained is filtered and the filtrate is diluted with ether to precipitate the sodium salt of N-[6-[p-(4-Piperidinopiperidino)phenyl]-1,2-dihydro-2-oxonicotinyl]ampicillin which is collected by filtration, washed with ether and dried; $[\alpha]_d^{25} + 79.8°$ (1.0% in methanol).

EXAMPLE 3

A suspension of 2.0 g. of sodium ampicillin in 50 ml. of N,N-dimethylacetamide is cooled and treated with 1.45 ml. of trimethylsilyl chloride and 0.8 ml. of triethylamine, and the mixture is stirred at room temperature for 1 hour. The resulting suspension is cooled and treated with 1.6 ml. of triethylamine followed by 1.79 g. of 6-[p-(dimethylamino)phenyl]-1,2-dihydro-2-oxonicotinyl chloride hydrochloride. The mixture is stirred at room temperature for 16 hours, then poured into 200 ml. of water. The mixture is adjusted to pH 8.1 with saturated aqueous sodium bicarbonate, then extracted several times with ethyl acetate, the extracts being discarded. The aqueous phase is acidified to pH 3.8 with 12% hydrochloric acid and the resulting precipitate of N-[6-[p-(dimethylamino)phenyl]-1,2-dihydro-2-oxonicotinyl]ampicillin is collected by filtration, washed with water and dried. This substituted ampicillin is dissolved in 30 ml. of N,N-dimethylacetamide and the solution is treated in turn with 1.6 ml. of a 50% solution of sodium 2-ethylhexanoate in 1-butanol, then with 100 ml. of ethyl acetate. The resulting precipitate of the sodium salt of N-[6-[p-(dimethylamino)phenyl]-1,2-dihydro-2-oxonicotinyl]ampicillin is collected by filtration, washed with ethyl acetate and dried; $[\alpha]_d^{25} + 134°$ (1% in methanol).

By substituting 1.79 g. of 6-[m-(dimethylamino)phenyl-1,2-dihydro-2-oxonicotinyl chloride hydrochloride for the 6-[p-(dimethylamino)phenyl]-1,2-dihydro-2-oxonicotinyl chloride, the product is N-[6-[m-(dimethylamino)-phenyl]-1,2-dihydro-2-oxonicotinyl]ampicillin, sodium salt; $[\alpha]_d^{25} + 139°$ (1.04% in methanol).

EXAMPLE 4

A solution of 2.25 g. of the triethylamine salt of ampicillin in 50 ml. of N,N-dimethylacetamide is cooled and treated with 1.25 ml. of trimethylsilyl chloride followed by 0.69 ml. of triethylamine, and the mixture is stirred at room temperature for 1 hour. The resulting suspension is cooled and treated with 1.38 ml. of triethylamine followed by 2.21 g. of 6-[p-(4-cyclohexyl-1-piperazinyl)phenyl]-1,2-dihydro-2-oxonicotinyl chloride hydrochloride. The mixture is stirred at room temperature for 16 hours, then poured into 200 ml. of water. The mixture is acidified to pH 3.8 with hydrochloric acid and the resulting precipitate of N-[6-[p-(4-cyclohexyl-1-piperazinyl)phenyl]1,2-dihydro-2-oxonicotinyl]ampicillin is collected by filtration, washed with water and dried. This substituted ampicillin is dissolved in 15 ml. of N,N-dimethylacetamide, the solution is filtered and the filtrate treated with 0.8 ml. of a 50% solution of sodium 2-ethylhexanoate in 1-butanol, then with 35 ml. of ethyl acetate. The resulting precipitate of the sodium salt of N-[6-[p-(4-cyclohexyl-1-piperazinyl)phenyl]-1,2-dihydro-2-oxonicotinyl]ampicillin, is collected by filtration, washed with ethyl acetate and dried; $[\alpha]_d^{25} + 132°$ (1% in methanol).

According to the above procedure, upon substituting in place of 6-[p-(4-cyclohexyl-1-piperazinyl)phenyl]-1,2-dihydro-2-oxonicotinyl chloride hydrochloride, an equivalent amount of:

6-[p-[4-(m-chlorophenyl)-1-piperazinyl]phenyl]-1,2-dihydro-2-oxonicotinyl chloride hydrochloride, 6-[p-(4-phenyl-1-piperazinyl)phenyl]-1,2-dihydro-2-nicotinyl chloride hydrochloride, 6-[p-[4-(1-pyrrolidinyl)piperidino]phenyl]-1,2--dihydro-2-oxonicotinyl chloride hydrochloride, 6-[p-(hexahydro-4-methyl-1H-1,4-diazepin-1-yl)-phenyl]-1,2-dihydro-2-oxonicotinyl chloride hydrochloride, 6-(piperidinophenyl)-1,2-dihydro-2-oxonicotinyl chloride hydrochloride and 6-[p-(4-methyl-1-piperazinyl)phenyl]-1,2-dihydro-1-methyl-2-oxonicotinyl chloride hydrochloride.

The following products are obtained:

N-[6-[p-[4-(m-chlorophenyl)-1-piperazinyl]phenyl]-1,2-dihydro-2-oxonicotinyl]ampicillin, N-[6-[p-(4-phenyl-1-piperazinyl)phenyl-1,2-dihydro-2-oxonicotinyl]ampicillin, N-[6-[p-[4-(1-pyrrolidinyl)piperidino]phenyl]-1,2-dihydro-2-oxonicotinyl]ampicillin, N-[6-[p-(hexahydro-4-methyl-1H-1,4-diazepin-1-yl)phenyl]-1,2-dihydro-2-oxonicotinyl]ampicillin, N-[6-(p-piperidinophenyl)-1,2-dihydro-2-oxonicotinyl]ampicillin and N-[6-[p-(4-methyl-1-piperazinyl)phenyl]-1,2-dihydro-1-methyl-2-oxonicotinyl]ampicillin, respectively.

EXAMPLE 5

Initially 1.81 ml. of trimethylsilyl chloride is added to a stirred suspension of 3.2 g. of the triethylamine salt of ampicillin in 130 ml. of tetrahydrofuran which is cooled to 0°–5° followed by the addition of 3.13 ml. of triethylamine. The mixture is stirred at 0°–5° for 15 minutes, then treated with 3.39 g. of 6-[p-(4-benzyl-1-piperazinyl)-phenyl]-1,2-dihydro-2-oxonicotinyl chloride hydrochloride and stirred at room temperature for 16 hours. The resulting precipitate is removed by filtration, washed with tetrahydrofuran and suspended in 200 ml. of water. The suspension is acidified to pH 5.8 with hydrochloric acid and the precipitate of N-[6-[p-(4-benzyl-1-piperazinyl)phenyl]-1,2-dihydro-2-oxonicotinyl]-ampicillin is collected by filtration, washed with water, then with ether and dried; $[\alpha]_d^{25}$ + 160° (1% in 3:1 dimethylformamide-pyridine).

EXAMPLE 6

Initially 3.8 ml. of trimethylsilyl chloride is added to a stirred suspension of 6.8 g. of the triethylamine salt of ampicillin in 250 ml. of tetrahydrofuran, which is cooled to 0°–5° followed by the addition of 6.72ml. of triethylamine. The mixture is stirred at 0°–5° for 30 minutes, then treated with 6.3 g. of 6-[p-(4-ethyl-1-piperazinyl)phenyl]-1,2-dihydro-2-oxonicotinyl chloride hydrochloride and stirred at room temperature for 16 hours. The reaction mixture is filtered and the filtrate is concentrated at reduced pressure and stirred with 300 ml. of water. The mixture is acidified to pH 5.6 with hydrochloric acid and the resulting precipitate of [6-[p-(4-ethyl-1-piperazinyl)-phenyl]-1,2-dihydro-2-oxonicotinyl]ampicillin is collected by filtration, washed with water, then with ether and dried; $[\alpha]_d^{25}$ + 179° (1.035% in 3:1 dimethylformamide-pyridine).

By substituting 5.94 g. of 6-[p-(4-propyl-1-piperazinyl)phenyl]-1,2-dihydro-2-oxonicotinyl chloride hydrochloride for the 6-[p-(4-ethyl-1-piperazinyl)phenyl]--1,2-dihydro-2-oxonicotinyl chloride hydrochloride, the product is N-[6-[p-(4-propyl-1-piperazinyl)-phenyl]-1,2-dihydro-2-oxonicotinyl]ampicillin; $[\alpha]_d^{25}$ + 196° (1.035% in 3:1 dimethylformamide-pyridine).

EXAMPLE 7

A suspension of 1.06g. of sodium ampicillin in 25 ml. of N,N-dimethylacetamide is cooled and treated with 0.73 ml. of trimethylsilyl chloride and 0.4 ml. of triethylamine, and the mixture is stirred at room temperature for 1 hour. The resulting suspension is cooled and treated with 0.8 ml. of triethylamine followed by 1.05 g. of 6-[o-(4-methyl-1-piperazinyl)phenyl]-1,2-dihydro-2-oxonicotinyl chloride hydrochloride. The mixture is stirred at room temperature for 16 hours, then poured into 100 ml of water. The pH of the mixture is adjusted to 8.1 with saturated aqueous sodium bicarbonate. The mixture is extracted three times with ethyl acetate and the extracts discarded. The resulting solution is acidified to pH 5.5 with dilute hydrochloric acid and then freeze dried. The residue is extracted with N,N-dimethylacetamide and the extract filtered. The filtrate is treated with 1.5 ml. of triethylamine followed by excess ethyl acetate/ether. The resulting precipitate of the triethylamine salt of N-[6-[o-(4-methyl-1-piperazinyl)-phenyl]-1,2-dihydro-2-oxonicotinyl-ampicillin is collected by centrifugation, washed with ether and dried; $[\alpha]_d^{25}$ + 118° (1.0% in 3:1 dimethylformamide-pyridine).

EXAMPLE 8

1,1'-carbonyldimidazole in the amount of 4.05 g. is added to a solution of 7.5 g. of 6-(p-morpholinophenyl)-1,2-dihydro-2-oxonicotinic acid in 46 ml. of N,N-dimethylacetamide, and the solution is warmed at 50°–60° for 2 hours or until carbon dioxide evolution ceases. The resulting solution of the acylimidazolide is cooled to 20°.

A suspenion of 11.25 g. of the triethylamine salt of ampicillin in 260 ml. of tetrahydrofuran is cooled to 5° and 6.4 ml. of trimethylsilyl chloride is added, followed by 3.5 ml. of triethylamine. The mixture is stirred at room temperature for 30 minutes and the resulting solution of disilated ampicillin (with suspended triethylamine hydrochloride) is cooled to 5°.

The above solutions of the acylimidazolide and disilylated ampicillin are mixed, stirred at room temperatures for 4.25 hours, then treated with 600 ml. of water and filtered. The filtrate is acidified to pH 2.2 with hydrochloric acid and extracted with ethyl acetate. The ethyl acetate extract, containing the acylated ampicillin, is dried and treated with 3.2 ml. of triethylamine. The precipitate of the triethylamine salt is collected by filtration and dissolved in water. The solution is acidified to pH 3.0 with hydrochloric acid and extracted with ethyl acetate. The ethyl acetate extract (containing the acylated ampicillin) is dried and treated with 2.0 ml. of a 50% solution of sodium 2-ethylhexanoate in 1-butanol. The resulting precipitate of N-[6-(p-morpholinophenyl)-1,2-dihydro-2-oxonicotinyl]ampicillin, sodium salt is collected by filtration, washed with ether and dried; $[\alpha]_d^{25}$ + 169° (1.01% in methanol).

EXAMPLE 9

A suspension of 44.1 g. of cephaloglycin dihydrate in 1.0 liter of chloroform is treated with 14 ml. of triethylamine and stirred at room temperature for 1 hour. The resulting solution is filtered and the filtrate evaporated at reduced pressure. The residue is triturated with ethyl acetate and the resulting solid triethylamine salt of cephaloglycin is removed by filtration and dried at reduced pressure over phosphorus pentoxide, $[\alpha]_d^{25}$ + 53° (1.04% in methanol).

A solution of 1.522 g. of the triethylamine salt of cephaloglycin in 15 ml. of N,N-dimethylacetamide is cooled to 0°-5°, treated with 0.76 ml. of trimethylsilyl chloride and 0.42 ml. of triethylamine, and stirred at room temperature for 1 hour. This solution of disilylated cephaloglycin is then added to a suspension of 1.104 g. of 6-[p-(4-methyl-1-piperazinyl)phenyl]-1,2-dihydro-2-oxonicotinyl chloride hydrochloride and 1.26 ml. of triethylamine in 30 ml. of N,N-dimethylacetamide, and the mixture is stirred at room temperature for 4 hours. The resulting mixture is filtered to remove triethylamine hydrochloride and the filtrate is diluted with excess ether. The resulting precipitate is collected by filtration, suspended in water and the mixture is basified to pH 8.2 with saturated aqueous sodium bicarbonate. The resulting solution is washed thoroughly with ethyl acetate, then acidified to pH 4.6 with hydrochloric acid. The resulting precipitate of N-[6-[p-(4-methyl-1-piperazinyl)phenyl]-1,2-dihydro-2-oxonicotinyl]cephaloglycin is collected by filtration, washed with water and dried. This substituted cephaloglycin is dissolved in 15 ml. of N,N-dimethylacetamide and the solution is treated with 0.6 ml. of 50% solution of sodium 2-ethylhexanoate in 1-butanol, then with excess ether. The resulting precipitate, the sodium salt of N-[6-[p-(4-methyl-1-pierazinyl)phenyl]-1,2dihydro--2-oxonicotinyl]cephaloglycin, is collected by filtration, washed with ether and dried; $[\alpha]_d^{25}$ + 42.5° (0.99% in methanol).

By substituting an equivalent amount of cephalexin hydrate for the cephaloglycin dihydrate in the above procedure, the product is N-[6-[p-(4-methyl-1-piperazinyl)-phenyl]-1,2-dihydro-2-oxonicotinyl]cephalexin. The sodium salt is formed in the usual manner.

EXAMPLE 10

A solution of 1.27 g. of the triethylamine salt of cephaloglycin in 20 ml. of N,N-dimethylacetamide is cooled to 0°-5°, treated with 0.64 ml. of trimethylsilyl chloride and 0.36 ml. of triethylamine, and stirred at room temperature for 1 hour. This solution of disilylated cephaloglycin is cooled and treated with 0.72 ml. of triethylamine followed by 930 mg. of 6-[o-(4-methyl-1-piperazinyl)phenyl]-1,2-dihydro-2-oxonicotinyl chloride hydrochloride. The mixture is stirred at room temperature for 16 hours, then poured into 100 ml. of water. The pH of the mixture is adjusted to 8.2 with saturated aqueous sodium bicarbonate. The mixture is extracted three times with ethyl acetate and the extracts discarded. The resulting solution is acidified to pH 5.5 with dilute hydrochloric acid. The resulting precipitate of N-[6-[o-(4-methyl-1-piperazinyl)phenyl]-1,2-dihydro-2-oxonicotinyl]cephaloglycin is collected by filtration, washed with water and dried. This substituted cephaloglycin is dissolved in 15 ml. of N,N-dimethylacetamide and the solution is treated with 0.5 ml. of a 50% solution of sodium 2-ethylhexanoate in 1-butanol, then with excess ethyl acetate/ether. The resulting precipitate of the sodium salt is collected by centrifugation, washed with ether and dried; $[\alpha]_d^{25}$ = 42° (1.0% in 3:1 dimethylformamide-pyridine).

According to the above procedure, upon substituting in place of 6-[o- (4-methyl-1-piperazinyl)phenyl]-1,2-dihydro-2-oxonicotinyl chloride hydrochloride, an equivalent amount of one of the following hydrochlorides:

6-[p-(dimethylamino)phenyl]-1,2-dihydro-2-oxonicotinyl chloride,
6-[m-(diethylamino)phenyl]-1,2-dihydro-2-oxonicotinyl chloride,
6-[p-(4-benzyl-1-piperazinyl)phenyl]-1,2-dihydro-2-oxonicotinyl chloride and
6-[p-(1-pyrrolidinyl)phenyl]-1,2-dihydro-2-oxonicotinyl chloride The sodium salts of the following products are obtained:

N-[6-[p-(dimethylamino)phenyl]-1,2-dihydro-2-oxonicotinyl]cephaloglycin
N-[6-[m-(diethylamino)phenyl]-1,2-dihydro-2-oxonicotinyl]cephaloglycin
N[-6-[p-(4-benzyl-1-piperazinyl)phenyl]-1,2-dihydro-2-oxonicotinyl]cephaloglycin and
N-[6-[p-(1-pyrrolidinyl)phenyl]-1,2-dihydro-2-oxonicotinyl]cephaloglycin, respectively.

By substituting an equivalent amount of cephalexin hydrate for the cephaloglycin dihydrate in the above procedure, the salts of the corresponding cephalexin derivatives are obtained:

EXAMPLE 11

A suspension of 922 mg. (2.62 mmole) of epicillin (contains 1.2% water) in 25 ml. N,N-dimethylacetamide is cooled in ice under nitrogen and 0.83 ml. (5.90 mmole) of trimethylamine is added, followed by 0.75 ml. (5.90 mmoles) of trimethylsilyl chloride.

After stirring for 1 hour at room temperature, the mixture is recooled in ice, and 965 mg. (2.62 mmoles) of 6-[p-(4-methyl-1-piperazinyl)phenyl]-1,2-dihydro-2-oxonicotinyl chloride hydrochloride is added, followed by 0.73 ml. (5.24 mmoles) of trimethylamine. After stirring for 1 hour at 0°, the mixture is allowed to stir at room temperature overnight. The mixture is next poured into water and the pH adjusted to 8.1 with saturated sodium bicarbonate solution. The material is next extracted three times with ethyl acetate, and the pH is brought to 3.5 with dilute hydrochloric acid. After standing overnight at 0°, there is collected 600 mg. of N-[6-[p-(4-methyl-1-piperazinyl)phenyl]-1,2-dihydro-2-oxonicotinyl]epicillin which is suspended in 10 ml. N,N-dimetylacetamide, and 0.7 ml. of sodium 2-ethylhexanoate (50% in n-butanol) is added, causing solution. A small amount of insoluble material is filtered off, and addition of ethyl ether to the filtrate causes the sodium salt of N-[6-[p-(4-methyl-1-piperazinyl)phenyl]-1,2-dihydro-2-oxonicotinyl]epicillin to precipitate. There is obtained 490 mg. of a yellow solid, $[\alpha]_D^{25}$ + 97.9° (c = 1.0% methanol). The pencillin assay is 89.4%.

EXAMPLE 12

A suspension of 900mg. (2.47 mmoles) of amoxicillin in 20 ml. N,N-dimethylacetamide is cooled in ice, and 1.03 ml. (7.41 mmoles) of triethylamine is added followed by 0.94 ml. (7.41 mmoles) of trimethylsilyl chloride. The mixture is allowed to stir at room temperature for 1 hour followed by recooling and the addition of 0.69 ml. (4.94 mmoles) of triethylamine. Next, 910 mg. (2.47 mmoles) of 6-[p-(4-methyl-1-piperazinyl)phenyl]-1,2-dihydro-2-oxonicotinyl chloride hydrochloride is added, and after ½ hour at 0°, the mixture is allowed to stir at room temperature overnight. The mixture is poured into water and the pH adjusted to 8.1 with saturated sodium bicarbonate solution. After extracting three times with ethyl acetate, the pH is brought to 5.8 with dilute hydrochloric acid. After cooling, there is collected 510 mg. of N-[6-[p-(4-methyl-1-piperazinyl)-phenyl]-1,2-dihydro-2-oxonicotinyl]amoxicillin, which is suspended in 10 ml. N,N-dimethylacetamide, and 0.8 ml. sodium 2-ethylhexanoate (50% in n-butanol) is added, causing solution. After filtering off a small amount of insoluble material, the filtrate is treated with ethyl acetate/ethyl ether causing the sodium salt of N-[6-[p-(4-methyl-1-piperazinyl)phenyl]-1,2-dihydro-2-oxonicotinyl]amoxicillin to precipitate. There is obtained 474 mg. of yellow solid, $[\alpha]_D^{25} + 140°$ ($c = 0.96\%$ in methanol). The pencillin assay is 78%.

EXAMPLE 13

A suspension of 1.77 g. (4.98 mmoles) of 6-[D-α-amino(2-thienyl)acetamido]penicillanic acid in 40 ml. of tetrahydrofuran is cooled in ice and 1.4 ml. (9.96 mmoles) of triethylamine added, followed by 1.26 ml. (9.96 mmoles) of trimethylsilyl chloride. The mixture is then allowed to stir at room temperature for 1 hour. The mixture is recooled and 1.4 ml. (9.94 mmoles) of triethylamine added, followed by 1.83 g. (4.98 mmoles) of 6-[p-(4-methyl-1-piperazinyl)phenyl]-1,2-dihydro-2-oxonicotinyl chloride hydrochloride. After stirring for 1 hour at 0°, the mixture is allowed to stir at room temperature overnight. The mixture is then poured into water and the pH adjusted to 8.1 with saturated sodium bicarbonate solution. After extracting three times with ethyl acetate, the aqueous solution is filtered and the pH adjusted to 4.0 with dilute hydrochloric acid. A yellow solid formed 6-[D-α-[6-[-p-(4-methyl-1-piperazinyl)-phenyl]-1,2-dihydro-2-oxonicotinamido]-(2-thienyl-)acetamido]penicillanic acid, which is collected and dried. This material is taken up in N,N-dimethylacetamide filtered to remove a small amount of solid, and 0.5 ml. sodium 2-ethylhexanoate (50% in n-butanol) is then added followed by ethyl ether causing the precipitate on the sodium salt of 6-[D-α-[6-[p-(4-methyl-1-piperazinyl)-phenyl]-1,2-dihydro-2-oxonicotinamido]-penicillanic acid. There is obtained 740 mg. of a yellow solid, $[\alpha]_D^{25} + 136°$ ($c = 1.0\%$ in DMSO). The penicillin assay is 61%.

EXAMPLE 14

One vial 1.05 g. of ampicillin, sodium salt is dissolved in 20 ml. N,N-dimethylacetamide. The solution is cooled in ice and 0.72 ml. (5.72 mmoles) of trimethylsilyl chloride added followed by 0.4 ml. (2.86 mmoles) of triethylamine. The cooling bath is removed and the mixture allowed to stir at room temperature for 1 hour. The mixture is recooled in ice and 1.0 ml. (7.16 mmoles) of triethylamine added, followed by 1.1 g. (2.86 mmoles) of 6-[m-(4-methyl-1-piperazinyl)phenyl]-1,2-dihydro-2-oxonicotinyl chloride hydrochloride. After stirring for 1 hour in ice, the mixture is allowed to stir at room temperature overnight. The mixture is then poured into water and the pH adjusted to 8.1 with saturated sodium bicarbonate solution. After extracting three times with ethyl acetate, the pH is brought to 4.0 with dilute hydrochloric acid. A yellow solid N-[6-[m-(4-methyl-1-piperazinyl)phenyl]-1,2-dihydro-2-oxonicotinyl]ampicillin is collected and dried. This is taken up in 15 ml. N,N-dimethylacetamide and 1.0 ml. of sodium 2-ethylhexanoate (50% in n-butanol) added. The addition of ethyl ether causes a yellow solid, the sodium salt of N-[6-[m-(4-methyl-1-piperazinyl)phenyl]-1,2-dihydro-2-oxonicotinyl]ampicillin to precipitate. The penicillin assay is 86.4%, $[\alpha]_D^{25} + 113°$ ($c = 1.01\%$ in methanol).

EXAMPLE 15

A suspension of 3.24 g. (3.95 mmoles) of cephaloglycin dihydrate (53.8% active ingredient) in 35 ml. N,N-dimethylacetamide is cooled in ice and 2.0 ml. (15.8 mmoles) of trimethylsilyl chloride added, followed by 2.2 ml. (15.8 mmoles) of triethylamine. After being allowed to stir at room temperature for 1 hour, the mixture is recooled and 1.528 g. (3.95 mmoles) of 6-[m-(4-methyl-1-piperazinyl)-phenyl]-1,2-dihydro-2-oxonicotinyl chloride hydrochloride is added followed by 1.38 ml. (9.88 mmoles) of triethylamine. The mixture is stirred for 1 hour at 0° and then allowed to stir at room temperature overnight. The mixture is poured into water and the pH adjusted to 8.1 with saturated sodium bicarbonate solution. The mixture is filtered, and the filtrate extracted three times with ethyl acetate. The pH is adjusted to 4.0 with dilute hydrochloric acid, and the precipitated solid N-[6-[m-(4-methyl-1-piperazinyl)phenyl]-1,2-dihydro-2-oxonicotinyl]cephaloglycin collected. This is suspended in 15 ml. of N,N-dimethylacetamide and 1.5 ml. of sodium 2-ethylhexanoate (50% in n-butanol) added, causing solution to occur, ethyl ether is then added and the precipitated sodium salt of N-[6-[m-(4-methyl-1-piperazinyl)phenyl]-1,2-dihydro-2-oxonicotinyl]cephaloglycin, which is collected and dried is (1.12 g.) $[\alpha]_D^{25} + 58°$ ($c = 1.03\%$ in methanol).

EXAMPLE 16

Ground tableted cephaloglycin (9.96 g.) (containing 4.41 g., 0.01 mole, cephaloglycin) is suspended in 60 ml. N,N-dimethylacetamide, cooled in ice and treated with 5.15 ml. (0.04 mole) of 98% trimethylsilyl chloride. When the temperature drops to 0°, 5.6 ml. of triethylamine is added. The suspension is stirred at room temperature for 1 hour, cooled and treated with 3.1 g. (0.01 mole) of 6-[m-(dimethylamino)phenyl]-2-oxo-1,2-dihydronicotinyl chloride hydrochloride dissolved in 60 ml. N,N-dimethylacetamide. Triethylamine (2.8 ml.) is added and the mixture is stirred overnight. The mixture is poured into 500 ml. ice-water mixture and the pH adjusted to 8 with saturated sodium bicarbonate solution, extracted with ethyl acetate and the separated aqueous layer acidified to pH 3.1 with dilute hydrochloric acid. The collected solid N-[6-[m-(dimethylamino)-phenyl]-1,2-dihydro-2-oxonicotinyl]cephaloglycin is washed thoroughly with water and then ether, dried briefly on the funnel then over phosphorus pentoxide in a vacuum desiccator with high vacuum (yield 4.0 g.). A 1 g. sample is dissolved in 10 ml. N,N-dimethylacetamide and 0.6 ml. of sodium 2-ethylhexanoate (50% in n-butanol) is added. The suspension is stirred 15 minutes and diluted with approximately 3 volumes of ethyl ether. The precipitated solid sodium salt of N-[6-[m-(dimethylamino)phenyl]-1,2-dihydro-2-oxonicotinyl]-cephaloglycin is separated by filtration, washed with ether and dried over phosphorus pentoxide under high vacuum (0.85 g.), $[\alpha]_D^{25} = +76$ (1.00% in 75% N,N-dimethylformamidepyridine) $\lambda = 347$, E $= 288$ (in pH containing 2.5% N,N-dimethylformamide). Cephalosporin assay 124%, 125%.

EXAMPLE 17

Triethylamine 0.57 ml. (4.03 mmoles) is added to a cold suspension of 1.5 g. (4.03 mmoles) of ampicillin, sodium salt in 50 ml. tetrahydrofuran, followed by 1.02 ml. (8.06 mmoles) of trimethylsilyl chloride. The mixture is allowed to stir at room temperature for 1 hour and then recooled in ice. Triethylamine 1.13 ml. (8.06 mmoles) is added, followed by 1.38 g. (4.03 mmoles) of 6-[m-(diethylamino)phenyl]-1,2-dihydro-2-oxonicotinyl chloride hydrochloride. After stirring for 1 hour at 0°, the mixture is allowed to stir at room temperature overnight. The mixture is then poured into water and the pH adjusted to 8.2 with saturated sodium bicarbonate solution. After extracting two times with ethyl acetate, the pH is adjusted to 4.4 with dilute hydrochloric acid. The precipitated solid N-[6-[m-(diethylamino)-phenyl]-1,2-dihydro-2-oxonicotinyl]ampicillin is collected and dried. This is taken up in N,N-dimethylacetamide and filtered to remove traces of solid, and 0.8 ml. of sodium 2-ethylhexanoate (50% in n-butanol) is added, and the sodium salt precipitated by the addition of ethyl acetate-/ethyl ether. There is obtained 1.2 g. of the yellow solid sodium salt of N-[6-[m-(diethylamino)phenyl]-1,2-dihydro-2-oxonicotinyl]-ampicillin, $[\alpha]_D^{25}$ +166° ($c$ = 1.02% in 75% N,N-dimethylformamide/25% pyridine). The penicillin assay is 109%.

EXAMPLE 18

A suspension of 3.61 g. (4.39 mmoles) of cephaloglycin, dihydrate (53.8% active ingredient) in 50 ml. tetrahydrofuran is cooled in ice and treated with 2.46 ml. (17.56 mmoles) of triethylamine followed by 2.22 ml. (17.56 mmoles) of trimethylsilyl chloride. The mixture is then allowed to stir at room temperature for 1 hour and then recooled. Triethylamine 1.23 ml. (8.78 mmoles) is next added followed by 1.5 g. (4.39 mmoles) of 6-[m-(diethylamino)phenyl]-1,2-dihydro-2-oxonicotinyl chloride hydrochloride. After 1 hour at 0°, the mixture is allowed to stir at room temperature overnight. The mixture is poured into water and adjusted to pH 8.1 with saturated sodium bicarbonate solution. After filtering to remove some solid, the tetrahydrofuran is removed under reduced pressure at room temperature. Adjusting the pH to 4.3 with dilute hydrochloric acid gives a yellow solid which is collected and dried. This is taken up in N,N-dimethylacetamide and a small amount of insoluble material is removed by filtration. Sodium 2-ethylhexanoate (50% in n-butanol) (1.1 ml.) is added, and the sodium salt of N-[6-[m-(diethylamino)-phenyl]-1,2-dihydro-2-oxonicotinyl]-cephaloglycin is precipitated in the form of a yellow solid by the addition of ethyl acetate/ethyl ether (1.54 g.), $[E]_D^{25}$ +72° ($c$ = 1.00% in 75% N,N-dimethylformamide/25% pyridine). The cephalosporin assay is 155%.

EXAMPLE 19

A suspension of 1.28 g. (2.38 mmoles) of amoxicillin, trihydrate (78% active ingredient) in 50 ml. tetrahydrofuran is cooled in ice and treated with 1.8 ml. (14.28 mmoles) of triethylamine. The mixture is allowed to stir at room temperature for 1 hour and then recooled in ice. 6-[m-(diethylamino)-phenyl]-1,2-dihydro-2-oxonicotinyl chloride hydrochloride 0.81 g. (2.38 mmoles) is added followed by 0.67 ml. (4.76 mmoles) of triethylamine. After 1 hour at 0°, the mixture is allowed to stir at room temperature overnight. The mixture is poured into water and the pH adjusted to 8.2 with saturated sodium bicarbonate solution. After extracting three times with ethyl acetate, the pH is adjusted to 4.0 and the yellow solid which formed is collected and dried. This is taken up in N,N-dimethylacetamide and small amounts of insoluble materials are removed by filtration. Sodium 2-ethylhexanoate (50% in n-butanol) (0.4 ml.) is added, and the sodium salt of N-[6-[m-(diethylamino)phenyl]-1,2-dihydro-2-oxonicotinyl]-amoxicillin precipitated by the addition of ethyl ether/ethyl acetate (610 mg.), $[\alpha]_D^{25}$ +124° ($c$ = 1.00% in methanol). The penicillin assay is 70.6%.

EXAMPLE 20

A cooled (10°) suspension of 0.687 g. (.0015 mole) of dry ampicillin triethylamine salt in 20 ml. tetrahydrofuran is treated with 0.407 ml. (0.0031 mole) of trimethylsilyl chloride and then 0.854 ml. triethylamine. The suspension is stirred at room temperature for 0.5 hours, then cooled in an ice bath and about 0.5 g. of 6-[p-(4-methyl-1-piperazinyl)phenyl]-1,2-dihydro-1-methyl-2-oxonicotinyl chloride hydrochloride is added. The reaction mixture is made basic with approximately 0.6 ml. triethylamine. The total additional tetrahydrofuran from washes is approximately 20 ml. The suspension is stirred overnight at room temperature and the suspended triethylamine salts are removed by filtration. A few drops of water is added to the filtrate, and it is evaporated to dryness in a rotating evaporator. The residue is suspended in 30 ml. cold water and 0.1N hydrochloric acid is added to bring the pH to 5.4. The yellow product N-[6-[p-(4-methyl-1-piperazinyl)-phenyl]-1,2-dihydro-1-methyl-2-oconicotinyl]ampicillin is collected by filtration and dried over phosphorus pentoxide in high vacuum (0.73 g.). λ 343 mμ E ¦ = 269 (pH 7 containing 2.5% N,N-dimethylformamide) $[\alpha]_D^{25}$ = +139° (1% in N,N-dimethylformamidepyridine, 3-1) colorimetric assay 94.4% as penicillin G.

EXAMPLE 21

Ampicillin triethylamine salt (2.25 g., .005 mole) is suspended in 100 ml. tetrahydrofuran, cooled to about 10° and treated with 1.25 ml. of trimethylsilyl chloride. The suspension is stirred for 10 minutes then 2.8 ml. of triethylamine is added. The mixture is stirred 30 minutes at room temperature, cooled, and treated with 2.01 g. (.005 mole) of freshly prepared 6-[3-chloro-4-(4-methyl-1-piperazinyl)-phenyl]-1,2-dihydro-2-oxonicotinyl chloride hydrochloride. An additional 50 ml. tetrahydrofuran was used in the transfer. The mixture is stirred at room temperature overnight and filtered. The filtrate is evaporated to dryness, the residue dissolved in water and acidified to a pH of 5 with dilute hydrochloric acid. The heavy fine precipitate of N-[6-[p-[3-chloro-4-(4-methyl-1-piperazinyl)]phenyl]-1,2-dihydro-2-oxonicotinyl]ampicillin is filtered off and triturated with a large volume of acetonitrile and again filtered. The solid product is dried in vacuo over phosphorus pentoxide (1.5 g.) $[\alpha]_D^{25}$ = 126° (1.045% in 3-1 N,N-dimethylformamide-pyridine).

EXAMPLE 22

2.48 g. (0.0055 mole) of ampicillin triethylamine salt is suspended in 70 ml. tetrahydrofuran with mechanical stirring. Trimethylsilyl chloride 1.1 g. and then triethylamine 2.81 ml. are added to the cooled suspension. The mixture is stirred at room temperature for 30 minutes, then cooled again while 6-[3-bromo-4-(4-methyl-1-piperazinyl)-phenyl]-4(or 5)-bromo-1,2-dihydro-2-oxonicotinyl chloride hydrochloride (freshly prepared from 2.36 g., 0.005 mole, of the acid) is added. The mixture is stirred overnight at room temperature and filtered. The filtrate is evaporated to dryness in a rotating evaporator. The residue is taken up in 100 ml. of water and stirred while adjusting the pH to 5, which resulted in the formation of a thick waxy suspension. The suspension is filtered, followed by removal of most of the liquid from the waxy solid. The solid is next extracted with a large amount of acetone, yielding 4.2 g. after filtering and drying the material. This solid is stirred in a large volume of acetonitrile and the fine solid is decanted from the dense particles on short settling. The extraction and decantation is repeated. The dense fraction of N-[6-[p-[3-bromo-4-(4-methyl-1-piperazinyl)]-phenyl]-4 (or 5)-bromo-1,2-dihydro-2-oxonicotinyl]ampicillin is collected by filtration and dried, yield 3.2 g., λ 360 mμ, E" = 176 (pH 7 buffer containing 2.5% N,N-dimethylformamide) $[\alpha]_D^{23}$ = 132° (1.04% in 3-1 N,N-dimethylformamidepyridine.

EXAMPLE 23

A suspension of 0.54 g. (1.08 mmoles) of 3-[[(5-methyl-1,3,4-thiadiazol-2-yl)thio]methyl]-7-(D-α-amino-α-phenylacetamido)-3-cephen-4-carboxylic acid is cooled in ice and 0.27 ml. (2.16 mmoles) of trimethylsilyl chloride added, followed by 0.15 ml. (1.08 mmoles) of triethylamine. The mixture is allowed to stir at room temperature for 1 hour. The mixture is recooled in ice and 0.4 g. (1.08 mmoles) of 6-[p-(4-methyl-1-piperazinyl)-phenyl]-1,2-dihydro-1-methyl-2-oxonicotinyl chloride hydrochloride added, followed by 0.3 ml. (2.16 mmoles) of triethylamine. After 1 hour at 0°, the mixture is allowed to stir at room temperature overnight. The mixture is poured into water and the pH adjusted to 8.1 with saturated sodium bicarbonate solution. After extracting three times with ethyl acetate, the pH is adjusted to 5.4 with dilute hydrochloric acid. A yellow solid precipitates which is collected and dried. The precipitate is taken up in N,N-dimethylacetamide, filtered, 0.15 ml. of sodium 2-ethylhexanoate (50% in n-butanol) added, and then ethyl ether/ethyl acetate added. The precipitated sodium salt of 3-[[(5-methyl-1,3,4-thiadiazol-2-yl)thio]-methyl]-7-[D-α-[6-[p-(4-methyl-1-piperazinyl)phenyl]-1,2-dihydro-2-oxonicotinamido]-α-phenylacetamido]-3-cephem-4-carboxylic acid is collected and dried, giving 250 mg. of a yellow solid, $[\alpha]_D^{25}$ +15° ($c$ = 1.01% in 75% N,N-dimethyl-formamide/25% pyridine). The cephalosporin assay is 91.4%.

EXAMPLE 24

A suspension of 1.0 g. (2.08 mmoles) of 3-[[(2-pyrimidinyl)thio]methyl]-7-(D-α-amino-α-phenylacetamido)-3-cephem-4-carboxylic acid in 25 ml. N,N-dimethylacetamide is cooled in ice and 0.29 ml. (2.08 mmoles) of triethylamine added, followed by 0.52 ml. (4.16 mmoles) of trimethylsilyl chloride. The mixture is allowed to stir at room temperature for 1 hour. The mixture is recooled in ice and 0.58 ml. (4.16 mmoles) of triethylamine added followed by 0.77 g. (2.08 mmoles) of 6-[p-(4-methyl-1-piperazinyl)phenyl]-1,2-dihydro-1-methyl-2-oxonicotinyl chloride hydrochloride. After stirring at 0° for 1 hour, the mixture is allowed to stir at room temperature overnight. The mixture is poured into water and the pH adjusted to 8.1 with saturated sodium bicarbonate solution. After extracting three times with ethyl acetate, the pH is adjusted to 5.4 with dilute hydrochloric acid. A yellow solid formed which was collected, dried, and taken up in N,N-dimethylacetamide followed by filtration. After the addition of 0.35 ml. of sodium 2-ethylhexanoate (50% in n-butanol) the sodium salt of 3-[[(2-pyrimidinyl)thio]methyl]-7-[D-α-[6-[p-4-methyl-1-piperazinyl)-phenyl]-1,2-dihydro-2-oxonicotinamido]-α-phenylacetamido]-3-cephem-4-carboxylic acid precipitated by the addition of ethyl ether/ethyl acetate. There is obtained 580 mg. of the sodium salt as a yellow solid, $[\alpha]_D^{25}$ +64° ($c$ = 1.03% in 75% N,N-dimethylformamide/25% pyridine). The cephalosporin assay is 93.8%.

EXAMPLE 25

Ampicillin 9 g. (0.020 mol) is silylated in tetrahydrofuran using trimethylsilyl chloride 5.36 ml. (0.04 mole) and triethylamine 8.4 ml. 6-(m-Nitrophenyl)-1,2-dihydro-2-oxonicotinyl chloride hydrochloride, prepared from reacting 5 g. of the acid with thionyl chloride, is added to the cooled suspension. An additional 0.5 equivalents of triethylamine is added and stirring is continued at room temperature overnight. The reaction mixture is filtered and the filtrate is evaporated to dryness. The residue (18 g. yellow solid) is suspended in water (200 ml.) and extracted with 300 ml. ethyl acetate as the pH is adjusted to 2.2 with 6N hydrochloric acid. The layers are separated and the aqueous layer is twice more extracted with 100 ml. ethyl acetate. The combined ethyl acetate extracts are dried with magnesium sulfate and evaporated to dryness to give N-[6-(m-nitrophenyl)-1,2-dihydro-2-oxonicotinyl]ampicillin (yield 12.1 g.). The solid is dissolved in a mixture of 50 ml. tetrahydrofuran and 35 ml. acetonitrile. The solution is treated with charcoal and filtered through a Supercel pad. The filtrate is poured into 800 ml. of ethyl ether containing 8 ml. of triethylamine. The pale yellow triethylamine salt is filtered off, washed with ether and dried over phosphorous pentoxide (10.58 g.) λ 345 E" = 293 $[\alpha]_D^{25}$ = −34° (1% in pH 7) colorimetric assay against penicillin G standard 122.8%.

EXAMPLE 26

A solution of 10 g. of triethylamine salt of N-[6-(m-nitrophenyl)-1,2-dihydro-2-oxonicotinyl]ampicillin in 100 ml. 1-1 tetrahydrofuran — water is reduced with 2 g. 20% palladium-on-barrium sulfate at room temperature and 50 pounds hydrogen pressure. The mixture is filtered and the black filtrate (contains catalyst colloid) is adjusted to approximately pH 2, filtered through charcoal and Supercel to give a dark yellow clear solution. The solution is adjusted to approximately pH 3.8 and the tetrahydrofuran removed in vacuo. The aqueous residue is extracted with 500 ml. of methyl ethyl ketone in two portions. The combined ketone extract is dried over magnesium sulfate and stored in the cold overnight. A solid is permitted to settle which is removed by decantation and filtration through filter aid. The filtrate is brought to pH 8.8 with triethylamine (determined on water diluted probes) and a dark syrup precipitated which is separated by decantation and discarded. The clear solution is filtered through Supercel and the filtrate is concentrated almost to dryness in vacuo. The syrup is diluted with 85 ml. chloroform and treated with 15 ml. (3 equivalents) of sodium 2-ethylhexanoate (50% in n-butanol). The result and precipitate is diluted with 250 ml. of ethyl ether and the solid is collected, washed with ether and dried, giving 5.35 g. The solid is dissolved in 60 ml. cold water and adjusted to pH 2.5 causing a fine solid N-[6-aminophenyl)-1,2-dihydro-2-oxonicotinyl]ampicillin to separate, which is washed with water and dried (yield 2.53 g. ), $[\alpha]_D^{25}$ = +169° (1.025% in 3-1 N,N-dimethylformamidepyridine) 88.1 and 82.2% penicillin G equivalents λ = 350

EXAMPLE 27

.0385 moles Cephaloglycin dihydrate (31.6 g. of 53.8% cephaloglycin from capsules) is silylated in an ice bath using 20.6 ml. (0.154 mole) trimethylsilyl chloride in 150 ml. N,N-dimethylacetamide and 21.6 ml. triethylamine. The thick suspension is diluted with 150 ml. tetrahydrofuran, stirred at room temperature for 1 hour, cooled to 5° and treated with .0385 moles of freshly prepared 6-(m-nitrophenyl)-1,2-dihydro-2-oxonicotinyl chloride hydrochloride. Enough triethylamine is added to bring the pH to above 7, and the suspension is stirred overnight. The pH is readjusted to 7 with triethylamine and insoluble material removed by filtration. The filtrate is poured into 700 ml. of cold water, adjusted to pH 6 with triethylamine and mixed with 500 ml. ethyl acetate. The resultant emulsion is filtered, the layers separated, again extracted with 500 ml. of ethyl acetate. The aqueous layer is mixed with 1 liter of ethyl acetate and is acidified to pH 2. The formed fine solid N-[6-(m-nitrophenyl)-1,2-dihydro-2-oxonicotinyl]cephaloglycin, which is collected by filtering both emulsified layers, is dried over phosphorous pentoxide in high vacuum (yield 6.45 g.) $[\alpha]_D^{25} = +49°$ (1.01% in 3-1 N,N-dimethylformamidepyridine).

EXAMPLE 28

N-[6-(m-Nitrophenyl)-1,2-dihydro-2-oxonicotinyl]-cephaloglycin (4 g.) and sodium bicarbonate (4 g.) in 125 ml. of water (cold) is adjusted to pH 8.5 with 6N sodium hydroxide causing the solids to slowly dissolve over a 30 minute period with the aid of stirring. Sodium dithionite (4.32 g.) was added to the mixture with the temperature being held at about 8° and sodium hydroxide added as needed to maintain pH of 3-8.5. After 1 hour, 6 ml. nitrobenzene is added to destroy excess sodium dithionite, the mixture is brought to pH 7 and extracted twice with ether (filter to break the emulsion). The aqueous layer is acidified to pH 3.8 and the fine solid N-[6-(m-aminophenyl)-1,2-dihydro-2-oxonicotinyl]cephaloglycin is collected by filtration (yield after drying 3 g.). This solid is finely ground in a 1—1 tetrahydrofuran-acetonitrile mixture containing 4% triethylamine filtered and the extraction is repeated several times. The combined extracts are evaporated to dryness in vacuo (below room temperature) (yield 2.52 g. of the triethylamine salt of N-[6-(m-aminophenyl)-1,2-dihydro-2-oxonicotinyl]cephaloglycin. This product is chromatographed over 150 g. of silica gel (4.5 cm. diameter) using 8% water 20% tetrahydrofuran 72% acetonitrile. The fractions containing product are identified by thin layer chromatography and are combined and evaporated to dryness (yield 1.31 g.) $[\alpha]_D^{25} = +63.5°$ (1% in 3-1 N,N-dimethylformamidepyridine) $\lambda = 350$ m$\mu$ E" = 286 (pH 7 containing 2.5% N,N-dimethylformamide. Assays 110% by cephalosporin assay.

EXAMPLE 29

A suspension of 1.28 g. (2.38 mmoles) of amoxicillin trihydrate (78% active component) in 50 ml. tetrahydrofuran is cooled in ice and treated with 1.81 ml. (14.28 mmoles) of trimethylsilyl chloride and 2.0 ml. (14.28 mmoles) of triethylamine. The mixture is allowed to stir at room temperature for 1 hour. The mixture is recooled in ice and 0.75 g. (2.38 mmoles) of 6-[m-(dimethylamino)phenyl]-1,2-dihydro-2-oxonicotinyl chloride hydrochloride is added, followed by 0.67 ml. (4.76 mmoles) of triethylamine. The mixture is stirred for 1 hour at 0°, then left stirring at room temperature overnight. The solvent is removed under reduced pressure and the residue taken up in water and the pH adjusted to 8.1 with saturated sodium bicarbonate solution. After extracting three times with ethyl acetate, the pH is adjusted to 3.8 with dilute hydrochloric acid, and the formed yellow-brown solid is collected and dried. This solid is dissolved in N,N-dimethylacetamide, and a small amount of insoluble material filtered off. Sodium 2-ethylhexanoate (50% in n-butanol) (0.6 ml.) is added and the sodium salt precipitated with ethyl ether/ethyl acetate. There is obtained 790 mg. of the yellow sodium salt of N-[6-[m-(dimethylamino)phenyl]-1,2-dihydro-2-oxonicotinyl]amoxicillin, $[\alpha]_D^{25} +115°$ ($c = 1.02\%$ in methanol). The penicillin assay is 60.7%.

EXAMPLE 30

Ampicillin triethylamine salt (2.7 g.) is suspended in 25 ml. tetrahydrofuran, cooled to 5°, 1.52 ml. of trimethylsilyl chloride is added and stirred for about 10 minutes followed by the addition of 3 ml. of triethylamine and the cooling bath removed for 30 minutes. Cooling is renewed and 1.8 g. of 6-[m-(1-pyrrolidinyl)phenyl]-1,2-dihydro-2-oxonicotinyl chloride hydrochloride is added with the reaction media temperature being maintained at about 2°. The mixture is stirred for 3 hours at room temperature and then filtered. The solid is washed 3 times with 15 ml. tetrahydrofuran and the combined tetrahydrofuran solution is evaporated to dryness at 40° in vacuo. The residue is mixed with ice water, adjusted to pH 8.5-9.0 with sodium hydroxide solution, and filtered through filter aid being careful to keep the solution cold. The filtrate is acidified with 1N hydrochloric acid to pH 2.5, and the precipitate collected by filtration and partly dried. The product is dissolved in 50 ml. 2-butanone, and the solution is dried with sodium sulfate and filtered. The filtate is mixed with 200 ml. of hexane to precipitate a dark brown solid. The solid is collected, air dried and extracted with 200 ml. of acetonitrile. The yellow extract is evaporated to dryness in vacuo to give N-[6-m-(1-pyrrolidinyl)-phenyl]-1,2-dihydro-2-oxonicotinyl]ampicillin (yield 0.19 g.), $[\alpha]_D^{25} = 188°$ (0.233% in 3-1 N,N-dimethylformamidepyridine) $\lambda = 342$ E" = 189 (in pH 7 buffer containing 2.5% N,N-dimethylformamide) Assayed 111%, 113.6 penicillin G equivalents colorimetrically.

EXAMPLE 31

Ampicillin triethylamine salt (3.72 g., 0.0083 mole) is suspended with stirring in 150 ml. tetrahydrofuran, cooled to 5° and treated with 2.1 ml. trimethylsilyl chloride. The solution is stirred for 10 minutes then triethylamine (4.7 ml.) is added. The cooling bath is removed and stirring is continued at room temperature for 30 minutes. The mixture is recooled to 2° and about 2.9 g. of 6-(m-piperidinophenyl)-1,2-dihydro-2-oxonicotinyl chloride hydrochloride is added. The suspension is stirred for 2 hours, the solid is removed by filtration, washed twice with 50 ml. tetrahydrofuran and the combined filtrates are evaporated to dryness in vacuo. The glassy residue is dissolved in water, adjusted to pH 9.5 (cool) with sodium hydroxide solution, insoluble material is removed by filtration and the cold filtrate acidified to pH 3-3.5. A yellow solid precipitates which is collected and washed twice with 100 ml. portions of water. The product N-[6-(m-piperidinophenyl)-1,2- dihydro-2-oxonicotinyl]-ampicillin is dried over phosphorus pentoxide, yielding 2.93 g., λ = 344 E" = 311 (in pH 7 buffer), [α]$_D^{25}$ +216° (1.04% in 3-1 N,N-dimethylformamidepyridine). Assay colorimetrically 96.6% as penicillin G.

EXAMPLE 32

A solution of ampicillin, sodium salt (1.05 g., 2.86 mmoles) is prepared by dissolving the salt in 20 ml. N,N-dimethylacetamide. The solution, which is cooled in ice, is treated with 0.72 ml. (5.72 mmoles) of trimethylsilyl chloride, followed by 0.4 ml. (2.86 mmoles) of triethylamine. The cooling bath is removed and the mixture allowed to stir at room temperature for 1 hour.

The mixture is recooled and 0.8 ml. (5.72 mmoles) of triethylamine added followed by 885 mg. of 6-[m-(methylamino)phenyl]-1,2-dihydro-2-oxonicotinyl chloride hydrochloride in portions over a ½ hour period. After stirring in ice for 1 hour, the mixture is allowed to stir at room temperature overnight. The mixture is poured into water and the pH adjusted to 8.1 with saturated sodium bicarbonate solution. After extracting 3 times with ethyl acetate, the pH is brought to 4.4 with dilute hydrochloric acid. A yellow solid formed which is collected, dried, taken up in 15 ml. N,N-dimethylacetamide and filtered to remove a small amount of insoluble material. Sodium 2-ethylhexanoate (50% in n-butanol) (1.0 ml.) is added, and upon the addition of ethyl ether the sodium salt of N-[6-[m-(methylamino)phenyl]-1,2-dihydro-2-oxonicotinyl]ampicillin precipitates. This is collected on the filter and washed with ethyl ether giving the sodium salt of N-[6-[m-(methylamino)-phenyl]-1,2-dihydro-2-oxonicotinyl]ampicillin.

EXAMPLE 33

A solution of 1.05 g. (2.86 mmoles) of ampicillin, sodium salt is prepared by dissolving the salt in 20 ml. N,N-dimethylacetamide. This solution is cooled in ice and treated with 0.72 ml. (5.72 mmoles) of trimethylsilyl chloride, followed by 0.4 ml. (2.86 mmoles) of triethylamine. The cooling bath is removed and the mixture allowed to stir at room temperature for 1 hour. The mixture is recooled and 0.8 ml. (5.72 mmoles) of triethylamine added. This is then treated with 935 mg. of 6-[m-(propylamino)phenyl]-1,2-dihydro-2-oxonicotinyl chloride hydrochloride in portions over a ½ hour period. After stirring in ice for 1 hour, the mixture is allowed to stir at room temperature overnight. The mixture is poured into water and the pH adjusted to 8.1 with saturated sodium bicarbonate solution. After extracing 3 times with ethyl acetate, the pH is brought to 4.4 with dilute hydrochloric acid yielding a yellow solid which is collected and dried. The solid is taken up in 15 ml. N,N-dimethylacetamide and 1.0 ml. of sodium 2-ethylhexanoate (50% in n-butanol) is added. After filtering to remove a trace of insoluble material, addition of ethyl ether causes the sodium salt of N-[6-[m-(propylamino)-phenyl]-1,2-dihydro-2-oxonicotinyl]ampicillin to precipitate. This compound is collected and washed with ethyl ether giving the desired penicillin in the form of its sodium salt.

EXAMPLE 34

M Aqueous mercuric perchlorate (5.0 ml.) is added to a solution of 1.55 g. of 3-(1-benzoylthiomethyl)-7-[D-α-[6-[p-(4-methyl-1-piperazinyl)phenyl]-1,2dihydro2-oxonicotinamido]-α-phenylacetamido]-3-cephem-4-carboxylic acid in 20 ml. of pyridine and 15 ml. of water at 50°, and the mixture is stirred at 50° for 45 minutes. The dark reaction mixture is diluted with 20 ml. of water, cooled in an ice bath, and treated with a brisk stream of hydrogen sulfide for 15 minutes. The filtered mixture is concentrated under reduced pressure to an amber gum and a separate aqueous phase of 5 ml. volume.

The gum is dissolved in 30 ml. of a solvent mixture consisting of 0.1M pyridine acetate in aqueous acetonitrile (1:1, vol) and chromatographed using the same solvent over 30 g. of SP-Sephadex in a 4 cm. diameter column. The desired fractions are combined and concentrated to a third of their orignal volume, and freeze-dried, yielding a yellow solid 3-(1-pyridylmethyl)-7-[D-α-[p-(4-methyl-1-piperazinyl)phenyl]-1,2-dihydro-2-oxonicotinamido]-α-phenylacetamido]-3-cephem-4-carboxylic acid betaine tetrahydrate, [α]$_D^{23}$ = +316° (1.02% in pH 7 buffer).

EXAMPLE 35

The final reaction mixture prepared according to the procedure described under Starting Materials (F), containing D-(+)-N-[6-[p-(4-methyl-1-piperazinyl)phenyl]-1,2-dihydro-2-oxonicotinyl]-2-phenylglycine, is treated with 22 ml. of N-methylmorpholine, cooled to -30°, treated with 11.5 ml. of ethyl chloroformate and stirred at -30° for 2 minutes. The mixture, containing the mixed anhydride of D-(+)-N-[6-[p-(4-methyl-1-piperazinyl)-phenyl-1,2-dihydro-2-oxonicotinyl]-2-phenylglycine and carbonic acid monoethyl ester, is treated with 100 ml. of a 1.06M solution of 6-amino-penicillanic acid trimethylsilyl ester [Glombitza, Ann. 673,166 (1964)]in dichloromethane. The mixture is stirred for 30 minutes at -30°, for 2 hours at room temperature, then diluted with 2.5 liters of ice water. The pH is adjusted, if necessary, to 5.8-6.8 with dilute aqueous sodium hydroxide and the mixture is stirred at 5° for 20 hours. The resulting precipitate of N-[6-[p-(4-methyl-1-piperazinyl)-phenyl]-1,2-dihydro-2-oxonicotinyl]ampicillin is collected by filtration, washed thoroughly with water and dried; [α]$_d^{25}$ + 163° (1.01% in 3:1 dimethylformamide-pyridine).

By substituting an equivalent amount of 7-aminocephalosporanic acid for the 6-aminopenicillanic acid in the above procedure, N-[6-[p-(4-methyl-1-piperazinyl)-phenyl]-1,2-dihydro-2-oxonicotinyl]cephaloglycin is obtained.

By substituting an equivalent amount of 7-amino-3-methylceph-3-em-4-carboxylic acid for the 6-aminopenicillanic acid, N-[6-[p-(4-methyl-1-piperazinyl)phenyl]-1,2-dihydro-2-oxonicotinyl]cephalexin is obtained.

By substituting an equivalent amount of one of the following
D-(+)-N-[6-[p-(4-methyl-1-piperazinyl)phenyl]-1,2-dihydro-2-oxonicotinyl]-2-(p-hydroxyphenyl)glycine
D-(+)-N-[6-[p-(4-methyl-1-piperazinyl)phenyl]-1,2-dihydro-2-oxonicotinyl]-2-(cyclohexa-1,4-dien-1-yl)-glycine
D-(+)-N-[6-[p-(4-ethyl-1-piperazinyl)phenyl]-1,2-dihydro-2-oxonicotinyl]-2-phenylglycine
D-(+)-N-[6-[p-(4-propyl-1-piperazinyl)phenyl]-1,2-dihydro-2-oxonicotinyl]-2-phenylglycine
D-(+)-N-[6-[p-[3-chloro-4-(4-methyl-1-piperazinyl)]-phenyl]-1,2-dihydro-2-oxonicotinyl]phenylglycine
D-(+)-N-[6-[m-(4-methyl-1-piperazinyl)phenyl]-1,2-dihydro-2-oxonicotinyl]-2-phenylglycine
D-(+)-N-[6-[m-(dimethylamino)phenyl]-1,2-dihydro-2-oxonicotinyl]phenylglycine D-(+)-N-[6-[m-(diethylamino)phenyl]-1,2-dihydro-2-oxonicotinyl]phenylglycine D-(+)-N-[6-[m-(dimethylamino)phenyl]-1,2-dihydro-2-oxonicotinyl](p-hydroxyphenyl)glycine D-(+)-N-[6-[m-(diethylamino)phenyl]-1,2-dihydro-2-oxonicotinyl](p-hydroxyphenyl)glycine D-(+)-N-[6-[m-(methylamino)phenyl]-1,2-dihydro-2-oconicotinyl]phenylglycine D-(+)-N-[6-[m-(n-propylamino)phenyl[-1,2-dihydro-2-oxonicotinyl]phenylglycine D-(+)-N-[6-[m-(amino)phenyl]-1,2-dihydro-2-oxonicotinyl]phenylglycine D-(+)-N-[6-[p-(4-benzyl-1-piperazinyl)phenyl]-1,2-dihydro-2-oxonicotinyl]-2-phenylglycine D-(+)-N-[6-[p-(4-cyclohexyl-1-piperazinyl)phenyl]-1,2-dihydro-2-oxonicotinyl]-2-phenylglycine, or D-(+)-N-[6-[p-(dimethylamino)phenyl]-1,2-dihydro-2-oxonicotinyl]phenylglycine in the place of D-(+)-N-[6-[p-(4-methyl-1-piperazinyl)phenyl]-1,2-dihydro-2-oxonicotinyl]-2-phenylglycine one obtains N-[6-[p-(4-methyl-1-piperazinyl)phenyl]-1,2-dihydro-2-oxonicotinyl]amoxicillin N-[6-[p-(4-methyl-1-piperazinyl)phenyl]-1,2-dihydro-2-oxonicotinyl]epicillin N-[6-[p-(4-ethyl-1-piperazinyl)phenyl]-1,2-dihydro-2-oxonicotinyl]ampicillin N-[6-[p-(4-n-propyl-1-piperazinyl)phenyl]-1,2-dihydro-2-oxonicotinyl]ampicillin N-[6-[p-[3-chloro-4-(4-methyl-1-piperazinyl)]-phenyl]-1,2-dihydro-2-oxonicotinyl]ampicillin N-[6-[m-(4-methyl-1-piperazinyl)phenyl]-1,2-dihydro-2-oxonicotinyl]ampicillin N-[6-[m-(dimethylamino)phenyl]-1,2-dihydro-2-oxonicotinyl]ampicillin N-[6-[m-(diethylamino)phenyl]-1,2-dihydro-2-oxonicotinyl]ampicillin N-[6-[m-(dimethylamino)phenyl]-1,2-dihydro-2-oxonicotinyl]amoxicillin N-[6-[m-(diethylamino)phenyl]-1,2-dihydro-2-oxonicotinyl]amoxicillin N-[6-[m-(methylamino)phenyl]-1,2-dihydro-2-oxonicotinyl]ampicillin N-[6-[m-(n-propylamino)phenyl]-1,2-dihydro-2-oxonicotinyl]ampicillin N-[6-(m-aminophenyl)-1,2-dihydro-2-oxonicotinyl]-ampicillin N-[6-[p-(4-benzyl-1-piperazinyl)phenyl]-1,2-dihydro-2-oxonicotinyl]ampicillin N-[6-[p-(4-cyclohexyl-1-piperazinyl)phenyl]-1,2-dihydro-2-oxonicotinyl]ampicillin N-[6-[p-(dimethylamino)phenyl]-1,2-dihydro-2-oxonicotinyl]ampicillin, respectively.

Starting Materials

The various starting materials employed in the foregoing examples and intermediates required for their preparation are obtained by the methods described in the following.

A. (SUBSTITUTED AMINO)ACETOPHENONES.

a. p-(4-Methyl-1-piperazinyl)acetophenone.

A solution of 1120 g. of N-methylpiperazine and 755 g. of p-fluoroacetophenone in 1920 ml. of dimethyl-sulfoxide is heated at 95° for 16 hours, then evaporated at reduced pressure. The residue is poured into 8 liters of water and the solution is basified with 440 g. of 50% aqueous sodium hydroxide and cooled. The precipitate of p-(4-methyl-1-piperazinyl)acetophenone is collected by filtration, washed with water and dried; m.p. 97°–99°.

b. p-(4-Propyl-1-piperazinyl)acetophenone.

A mixture of 33.2 g. of p-fluoroacetophenone, 48.3 g. of N-propylpiperazine and 99.5 g. of potassium carbonate in 100 ml. of dimethyl sulfoxide is stirred and heated at 95° for 4.5 hours, then cooled and poured into ice water. The precipitate of p-(4-propyl-1-piperazinyl)-acetophenone is collected by filtration, washed with water and dried; m.p. 68°–70° after crystallization from hexane.

c. o-(4-Methyl-1-piperazinyl)acetophenone.

A mixture of 55.2 g. of o-fluoroacetophenone and 100 ml. of N-methyl-piperazine is heated at 95°–100° for 19 hours, then cooled and poured into 1600 ml. of water containing 22 ml. of 50% aqueous sodium hydroxide. The mixture is extracted with three 300 ml. portions of ether. The combined ether extract is washed thoroughly with water, then with saturated aqueous sodium chloride, dried and evaporated to give o-(4-methyl-1-piperazinyl)acetophenone as a viscous oil, suitable for use without further purification.

d. m-(4-Methyl-1-piperazinyl)acetophenone.

m-Fluoroacetophenone 101 g. (0.732 mole) is added dropwise to 500 ml. of nitric acid (90% fuming) cooled to −10°. The rate of addition is adjusted so that the temperature remains below −5°. After stirring for ½ hour at <5°, the solution is stirred at 3° for ½ hour, and then poured into 2.5 liters of water. An oil forms which solidifies on standing. The produce is collected and recrystallized from ethanol/water. There is obtained 94.9 g. (70.8%) of 2'-nitro-5'-fluoroacetophenone, m.p. 49°–52°.

A solution of 54.9 g. (0.3 mole) of 2'-nitro-5'-fluoroacetophenone in 500 ml. of dimethyl sulfoxide is treated with 60 g. (0.6 mole) of N-methylpiperazine. The solution becomes slightly warm, and after stirring for 1 hour at room temperature, 225 ml. of 2N sodium hydroxide (0.45 mole) is added, and the solution then poured into excess water, a solid separates which is collected and dried. Recrystallization from benzene/hexane gives 52.2 g. (66.2%) of 2'-nitro-5'-(4-methyl-1-piperazinyl)-acetophenone, m.p. 91.5°–92.5°.

A solution of 51.4 g. (0.195 mole) of 2'-nitro-5'-(4-methyl-1-piperazinyl)acetophenone in 500 ml. benzene is treated with 1 g. of 5% Pt/C and reduced at room temperature, 50 psi. The vigorous reduction causes the temperature to rise to 62°. When the required amount of hydrogen is taken up, the reaction mixture is filtered and the solvent removed under reduced pressure leaving 45.5 g. (100%) of a dark oil which solidifies on standing. The crude 2'-amino-5'-(4-methyl-1-piperazinyl)acetophenone is used directly in the following step.

A solution of 8.46 g. (0.036 mole) of crude 2'-amino-5'-(4-methyl-1-piperazinyl)acetophenone is dissolved in 85 ml. of ab ethanol and 8.5 ml. of concentrated sulfuric acid added. The mixture becomes gummy. On heating at reflux for a few minutes, the gum dissolves and a brown solid appears. The boiling mixture is treated in portions with 5.0 g. (0.072 mole) of solid sodium nitrite. After all has been added, the mixture is heated at reflux for 45 minutes. The mixture is poured into water, made basic with 50% sodium hydroxide, and extracted three times with chloroform. The combined chloroform extracts are washed with saturated sodium chloride, dried over sodium sulfate, and the solvent removed under reduced pressure leaving a dark oil. Two distillations under reduced pressure through a short path distillation column using a heat lamp give 4.07 g. (51.4%) of the pure m-(4-methyl-1-piperazinyl)acetophenone as a golden oil, b.p. 150°–180°/0.4 mm.

e. m-(Diethylamino)acetophenone.

A solution of 100.3 g. (0.744 mole) of m-aminoacetophenone in 600 ml. of absolute ethanol is treated with 85 ml. acetaldehyde, 10 ml. acetic acid, 3 g. platinum oxide, and reduced at 43°, 66 pounds per square inch. The solution is then filtered, and the ethanol removed under reduced pressure. The residue is taken up in chloroform, washed with 5% sodium hydroxide, then with water. Drying over sodium sulfate and removal of the solvent under reduced pressure gives an oil. This is twice distilled through a short-path column, b.p. 122°–128°/2.1 mm. There is obtained 62.6 g. of a yellow oil which is a mixture of mono- and dialkylated material. This material is resubmitted to the reductive alkylation conditions as described above. Identical workup gives the crude product. Two distillations through a short-path column gives 35.3 g. of m-(diethylamino)acetophenone as a yellow oil, b.p. 87°–92°/0.3 mm.

f. 3'-Chloro-4'-(4-methyl-1-piperazinyl)acetophenone.

3',4'-Dichloroacetophenone (9.65 g., 0.05 mole) and N-methylpiperazine (10 g., 0.1 mole) are refluxed (165° C) for 24 hours. The solution is cooled and 100 ml. water containing 2 g. of sodium hydroxide is added. The oil is decanted and diluted with 200 ml. of toluene and washed first with dilute alkali then several times with water. The toluene layer is dried with magnesium sulfate and evaporated in vacuo to an oil. The residue is distilled 146°–150° at 0.1–0.3 mm., yield 3.0 g. This product is dissolved in ethyl ether and converted to the hydrochloride using isopropanolic hydrogen chloride and the salt crystallized from acetonitrile. The purified salt is reconverted to the base with dilute sodium hydroxide. The product is extracted using ethyl ether, separated, dried, evaporated to dryness to give 3'-chloro-4'-(4-methyl-1-piperazinyl)acetophenone as a yellow oil.

g. m-(1-Pyrrolidinyl)acetophenone

2'-Nitro-5'-fluoroacetophenone (36.6 g., 0.2 mole) is reacted with 28.4 g. (0.4 mole) pyrrolidine at room temperature is 300 ml. DMSO (exothermic). The mixture is stirred for 1 hour 40 minutes (yellow solid crystallizes), then poured into 1 liter water containing 12 g. (0.3 mole) sodium hydroxide. The solid 2'-nitro-5'-(1-pyrrolidinyl)acetophenone is collected by filtration, washed with water and dried. After crystallization from benzene, 41.1 g. of product is obtained, m.p. 134°–135°.

2-Nitro-5-(1-pyrrolidinyl)acetophenone (2.35 g., 0.01 mole) is reduced in benzene using 0.2 g. of 5% palladium-on-carbon. The reaction mixture is filtered from the catalyst and evaporated to dryness (reduced pressure). The solid is dissolved in N, hydrochloric acid and reprecipitated with N, sodium hydroxide. The resulting dark brown solid 2'-amino-5'-(1-pyrrolidinyl)- acetophenone is collected and dried. After crystallization from hot hexane, 0.5 g., of product is obtained, m.p. 86.5°–87.5°.

2-Amino-5-(1-pyrrolidinyl)acetophenone (from reduction of 0.15 mole of nitro compound) in 350 ml. ethanol (directly from reduction) is treated with 35 ml. 97% sulfuric acid and brought to reflux. A total of 20.7 g. (0.3 mole) of sodium nitrite is added in small portions to the refluxing solution over 2 hours. The refluxing is continued an additional 1 hour and the mixture is poured into 1 liter of water which contained 6 g. of sodium hydroxide. The resulting aqueous solution is extracted with chloroform several times, the combined chloroform layers are washed with saturated sodium chloride. The chloroform layer is dried and evaporated to dryness. The residue is distilled at 150°–160°/1.5-2.0 mm. to give 4.7 g. of m-(1-pyrrolidinyl)- acetophenone $\lambda = 372$ m$\mu$ E" = 109 (in methanol).

h. m-Piperidinylacetophenone.

2'-Nitro-5'-fluoroacetophenone (36.6 g., 0.2 mole) is dissolved in 56 ml. DMSO and added dropwise to 39.5 ml. (0.4 mole) piperidine in 100 ml. DMSO (temperature rose to 55° exothermically). After 40 minutes, the clear solution is poured into 1 liter of water containing 12 g. sodium hydroxide. The bright yellow solid 2'-nitro-5'-piperidinoacetophenone is collected by filtration, washed with water and dried over phosphorus pentoxide in vacuo overnight. After recrystallized from ethyl acetate/petroleum ether, 44.95 g. of product is obtained, 100.5°–101.5°. $\lambda = 400$ E" = 792 (methanol)

2'-Nitro-5'-piperidinylacetophenone (44.5 g.) in 450 ml. benzene is reduced with hydrogen catalytically using 2 g. 5% platinum-on-carbon. The catalyst is filtered off and the filtrate evaporated in vacuo to a dark residue which solidifies on cooling. This solid is dissolved in benzene and extracted with excess 1N-hydrochloric acid in several portions. The combined extracts are basified with sodium hydroxide, the yellow solid is filtered off and washed several times with water. The product 2'-amino-5'-piperidinoacetophenone is dried over phosphorus pentoxide in vacuo giving 35.77 g., m.p. 60°–61°. $\lambda = 388$ E" = 179 (in methanol)

2'-Amino-5'-piperidinoacetophenone (1.64 g., 0.075 mole) is dissolved in 20 ml. ethanol at 0°, followed by the addition of 2 ml. of 97% sulfuric acid then, slowly, a solution of 1.1 g. sodium nitrite in 1 ml. water. This solution is added dropwise to 130 ml. ethanol at 60°. Heating is continued for 30 minutes, 200 ml. water is added and the solution is basified to pH about 10 with sodium hydroxide. The resulting mixture is extracted with ethyl ether, the ether separated and evaporated to dryness. The resulting 1.2 g. of oil was distilled at 133°–140°/0.1-0.3 mm. to give 0.5 g. a yellow oil, m-piperidinylacetophenone.

i. m-(Methylamino)acetophenone

A solution of 13.5 g. (0.1 mole) of m-aminoacetophenone in 100 ml. pyridine is cooled in ice and treated dropwise with 14.9 ml. (0.105 mole) of trifluoroacetic anhydride. The solution is stirred in ice for 45 minutes, then poured into water. The crude solid is collected and dried. Recrystallization from ethanol/water using charcoal gives 14.0 g. of a white solid m-(trifluoroacetamido)acetophenone, m.p. 130°–131.5°.

A solution of 14.0 g. (0.06 mole) of m-(trifluoroacetamido)acetophenone in 300 ml. acetone containing 15.6 ml. (0.25 mole) of methyl iodide is warmed to almost boiling and 14.0 g. (0.25 mole) of powdered potassium hydroxide added. After refluxing for 10 minutes, the solution is decanted from the potassium hydroxide, and the excess acetone and methyl iodide removed under reduced pressure. The residue is treated with a solution of 14 g. potassium hydroxide in 300 ml. water and heated at reflux for 10 minutes. The solution is extracted two times with chloroform and the chloroform washed with water. After drying over magnesium sulfate, the solvent is removed under reduced pressure leaving an oil. This is distilled at 98°–105°/0.5 mm. giving 8.0 g. of the product m-(methylamino)- acetophenone as a yellow oil.

j. m-(Propylamino)acetophenone

A solution of 13.5 g. (0.1 mole) of m-aminoacetophenone in 150 ml. methanol is treated with 5.8 g. of propionaldehyde and stirred at room temperature for 1 hour. 0.5 g. of 5% platinum-on-carbon is added and the mixture reduced at 24°, 50 pounds per square inch. When the required amount of hydrogen has been taken up the reduction is stopped and the mixture filtered to remove catalyst. The methanol is removed under reduced pressure and the residue taken up in chloroform. This is washed with 5% sodium hydroxide, then water. Drying over magnesium sulfate and removal of the solvent under reduced pressure gives the crude product. Distillation at 108°–122°/0.5 mm. gives 13.8 g. of m-(propylamino)-acetophenone as a yellow oil.

B.
6-SUBSTITUTED-1,2-DIHYDRO-2-OXONICOTINONITRILES.

a.
6-[p-(4-Methyl-1-piperazinyl)phenyl]-1,2-dihydro-2-oxonicotinonitrile.

To a stirred suspension of 820 g. of sodium methoxide in 7.5 liters of tetrahydrofuran is added dropwise a solution of 918 g. of ethyl formate and 2.7 kg. of p-(4-methyl-1-piperazinyl)acetopenone in 7 liters of tetrahydrofuran while maintaining the temperature below 11°. The mixture is diluted further with 4 liters of tetrahydrofuran and stirred at room temperature for 16 hours. The resulting precipitate of the sodium salt of p-(4-methyl-1-piperazinyl)benzoylacetaldehyde is collected by filtration, washed with tetrahydrofuran and dried. A solution of this sodium salt in 12 liters of water is treated with 1050 g. of 2-cyanoacetamide and a solution consisting of 130 ml. of acetic acid, 300 ml. of water and 230 ml. of piperidine. The solution is stirred and heated, while allowing tetrahydrofuran to distill until the temperature reaches 92°, and is maintained at this temperature for 3 hours, then allowed to stand at room temperature for 16 hours. The mixture is acidified to pH 6 with acetic acid, then neutralized to pH 7.1 with saturated aqueous sodium bicarbonate. The precipitate of 6-[p-(4-methyl-1-piperazinyl)phenyl]-1,2-dihydro-2-oxonicotinonitrile is collected by filtration, washed with water and dried; m.p. <310° (dec.).

In a similar manner, the following nitriles are prepared:

b.
6-[p-(Dimethylamino)phenyl]-1,2-dihydro-2-oxonicotinonitrile.

From a solution of the sodium salt of p-(dimethylamino)benzoylacetaldehyde in 400 ml. of water (prepared from 11.4 g. of sodium methoxide in 100 ml. of tetrahydrofuran and a solution of 29.3 g. of p-(dimethylamino)acetophenone [J.A.C.S. 73, 864 (1951) and 13.3 g. of ethyl formate in 130 ml. of tetrahydrofuran), 18.5 g. of 2-cyanoacetamide and a solution consisting of 2.3 ml. of acetic acid, 5.2 ml. of water and 4.0 ml. of piperidine, there is obtained 6-[p-(dimethylamino)phenyl]-1,2-dihydro-2-oxonicotinonitrile; m.p. 280°–292° (dec.) after crystallization from aqueous dimethyl sulfoxide.

c.
6-[m-Dimethylamino)phenyl]-1,2-dihydro-2-oxonicotinonitrile.

By substituting the same amount of m-(dimethylamino)acetophenone [Compt. rend. 235, 546 (1952)] for the p-(dimethylamino)acetophenone in b) above, the product obtained is 6-[m-(dimethylamino)phenyl]-1,2-dihydro-2-oxonicotinonitrile; m.p. > 260° (dec.).

d.
6-[p-4-Propyl-1-piperazinyl)phenyl]-1,2-dihydro-2-oxonicotinonitrile.

From a solution of the sodium salt of p-(4-propyl-1-piperazinyl)benzoylacetaldehyde in 150 ml. of water (prepared from 5.7 g. of sodium methoxide in 500 ml. of tetrahydrofuran, and a solution of 24.6 g. of p-(4-propyl-1-piperazinyl)acetophenone and 8.0 ml. of ethyl formate in 100 ml. of tetrahydrofuran), 8.4 g. of 2-cyanoacetamide and a solution consisting of 0.95 ml. of acetic acid, 4.0 ml. of water and 0.9 ml. of piperidine, there is obtained 6-[p-(4-propyl-1-piperazinyl)phenyl]-1,2-dihydro-2-oxonicotinonitrile; m.p. 288°–290° (dec.).

e.
6-(p-Piperidinophenyl)-1,2-dihydro-2-oxonicotinonitrile.

From a solution of the sodium salt of p-(piperidino)benzoylacetaldehyde in 300 ml. of water (prepared from 11.4 g. of sodium methoxide in 100 ml. of tetrahydrofuran, and a solution of 36.5 g. of p-(piperidino)acetophenone and 13.3 g. of ethyl formate in 130 ml. of tetrahydrofuran), 18.9 g. of 2-cyanoacetamide and a solution consisting of 2.3 ml. of acetic acid, 5.3 ml. of ester and 4.1 ml. of piperidine, there is obtained 6-(p-piperidinophenyl)-1,2-dihydro-2-oxonicotinonitrile.

f.
6-(p-Morpholinophenyl)-1,2-dihydro-2-oxonicotinonitrile.

To a stirred mixture of 38.8 g. of a 57% sodium hydride dispersion in mineral oil and 500 ml. of benzene is added dropwise with cooling a solution of 82.1 g. of p-(morpholino)acetophenone (Brit. Pat. 911,342), 45 ml. of ethyl formate and 2 ml. of ethanol in 300 ml. of benzene. An additional 400 ml. of benzene is added and the suspension is stirred at room temperature for 16 hours, then treated with 1.5 liters of cold water. The aqueous phase, containing the sodium salt of p-(morpholino)benzoylacetaldehyde, is separated and treated successively with 28.6 ml. of acetic acid, 10 ml. of piperidine and 34 g. of 2-cyanoacetamide. The mixture is stirred and heated at reflux for 3 hours, cooled and acidified with acetic acid to pH 5.0. The resulting precipitate of 6-(p-morpholinophenyl)-1,2-dihydro-2-oxonicotinonitrile is collected and triturated with ethyl acetate; m.p. 272°–275° after two crystallizations from ethanol.

g.
6-[p-(4-Piperidinopiperidino)phenyl]-1,2-dihydro-2-oxonicotinonitrile.

A mixture of 10.7 g. of 6-(p-fluorophenyl)-1,2-dihydro-2-oxonicotinonitrile [J. Med. Chem. 14, 342 (1971)] and 16.8 g. of 4-piperidinopiperidine in 140 ml. of dimethyl sulfoxide is stirred and heated at 95°-100° for 50 hours. The mixture is cooled and diluted with 450 ml. of 95% ethanol. The resulting precipitate of 6-[p-(4-piperidinopiperidino)phenyl]-1,2-dihydro-2-oxonicotinonitrile is collected by filtration, washed with 95% ethanol and dried; m.p. 288°-293° (dec.).

In a similar manner, the following nitriles are prepared:

h.
6-[p-(4-Cyclohexyl-1-piperazinyl)phenyl]-1,2-dihydro-2-oxonicotinonitrile.

From 11.7 g. of 6-(p-fluorophenyl)-1,2-dihydro-2-oxonicotinonitrile and 18.4 g. of N-cyclohexylpiperazine in 150 ml. of dimethyl sulfoxide, there is obtained 6-[p-(4-cyclohexyl-1-piperazinyl)phenyl]-1,2-dihydro-2-oxonicotinontrile; m.p. 306°-312° (dec.).

i.
6-[p-(4-Benzyl-1-piperazinyl)phenyl]-1,2-dihydro-2-oxonicotinonitrile.

From 11.7 g. of 6-(p-fluorophenyl)-1,2-dihydro-2-oxonicotinonitrile and 19.1 g. of N-benzylpiperazine in 150 ml. of dimethyl sulfoxide, there is obtained 6-[p-(4-benzyl-1-piperazinyl)phenyl]-1,2-dihydro-2-oxonicotinonitrile; m.p. 275°-286° (dec.).

j.
6-[p-(4-Ethyl-1-piperazinyl)phenyl]-1,2-dihydro-2-oxonicotinonitrile.

From 21.4 g. of 6-(p-fluorophenyl)-1,2-dihydro-2-oxonicotinonitrile and 22.8 g. of N-ethylpiperazine in 200 ml. of dimethyl sulfoxide, there is obtained 6-[p-(4-ethyl-1-piperazinyl)phenyl]-1,2-dihydro-2-oxonicotinonitrile; m.p. 283°-285° (dec.).

k.
6-[p-[4-(m-Chlorophenyl)-1-piperazinyl]phenyl]-1,2-dihydro-2-oxonicotinonitrile.

From 12.9 g. of 6-(p-fluorophenyl)-1,2-dihydro-2-oxonicotinonitrile and 23.7 g. of N-(m-chlorophenyl)-piperazine in 180 ml. of dimethyl sulfoxide; there is obtained 6-[p-[4-(m-chlorophenyl)-1-piperazinyl]phenyl]-1,2-dihydro-2-oxonicotinonitrile.

l.
6-[p-(4-Phenyl-1-piperazinyl)phenyl]-1,2-dihydro-2-oxonicotinonitrile.

From 12.9 g. of 6-(p-fluorophenyl)-1,2-dihydro-2-oxonicotinonitrile and 19.5 g. of N-phenylpiperazine in 180 ml. of dimethyl sulfoxide, there is obtained 6-[p-(4-phenyl-1-piperazinyl(phenyl]-1,2-dihydro-2-oxonicotinonitrile.

m.
6-[p-[4-(1-Pyrrolidinyl)piperidino]phenyl]-1,2-dihydro-2-oxonicotinonitrile.

From 11.7 g. of 6-(p-fluorophenyl)-1,2-dihydro-2-oxonicotinonitrile and 16.7 g. of 4-(1-pyrrolidinyl)-piperidine in 150 ml. of dimethyl sulfoxide, there is obtained 6-[p-[4-(1-pyrrolidinyl)piperidino]phenyl]-1,2-dihydro-2-oxonicotinonitrile; m.p. 318°-326° (dec.).

n.
6-[p-(Hexahydro-4-methyl-1H-1,4-diazepin-1-yl)phenyl]-1,2-dihydro-2-oxonicotinonitrile.

From 12.9 g. of 6-(p-fluorophenyl)-1,2-dihydro-2-oxonicotinonitrile and 13.8 g. of N-methylhomopiperazine in 180 ml. of dimethyl sulfoxide, there is obtained 6-[p-hexahydro-4-methyl-1H-1,4-diazepin-1-yl)phenyl]-1,2-dihydro-2-oxonicotinonitrile.

o.
6-[m-(4-Methyl-1-piperazinyl)phenyl]-1,2-dihydro-2-oxonicotinonitrile.

A suspension of 5.3 g. (0.098 mole) of sodium methoxide in 100 ml. ethyl ether under nitrogen is cooled to 3° and treated dropwise with a solution of 18.4 g. (0.084 mole) of m-(4-methyl-1-piperazinyl)acetophenone and 6.25 g. (0.084 mole) of ethyl formate in 100 ml. ethyl ether while keeping the temperature below 5°. When the addition is completed, the mixture is allowed to stir at room temperature overnight. 100 ml. water is then added and the layers separated. The ethyl ether layer is washed with an additional 75 ml. of water. The pH of the aqueous layer is adjusted to pH 9 with acetic acid. 10.6 g. (0.126 mole) of cyanoacetamide is then added and the solution heated at 90° for 6 hours. A solid formed which is collected and dried. Recrystallization from DMSO/water gives 14.8 g. (60.2%) of pure 6-m-(4-methyl-1-piperazinyl)-phenyl]-1,2-dihydro-2-oxonicotinonitrile, m.p. 264°-267° d., as a yellow solid.

p.
6-[o-(4-Methyl-1-piperazinyl)phenyl]-1,2-dihydro-2-oxonicotinonitrile.

To a stirred suspension of 22.9 g. of sodium methoxide in 500 ml. of dry ether is added dropwise at 7°-10° a solution of 40.3 g. of ethyl formate and 79.3 g. of o-(4-methyl-1-piperazinyl)acetophenone in 150 ml. of dry ether. The mixture is stirred at room temperature for 17 hours, then extracted three times with 300 ml. portions of water. The combined aqueous extract, containing the sodium salt of o-(4-methyl-1-piperazinyl)-benzoylacetaldehyde, is adjusted to pH 9 with acetic acid, treated with 45.8 g. of 2-cyanoacetamide and stirred and heated at 90°-95° for 6 hours. The mixture is cooled and the pricipitate of 6-[o-(4-methyl-1-piperazinyl)phenyl]-1,2-dihydro-2-oxonicotinonitrile is collected by filtration, washed with water and dried; m.p. 202°-203° after crystallization from ethyl acetate.

q.
6-[m-(Diethylamino)phenyl]-1,2-dihydro-2-oxonicotinonitrile.

A suspension of 10.9 g. (0.202 mole) of sodium methoxide in 200 ml. ethyl ether is cooled to 3° and treated dropwise with a solution of 35.2 g. (0.184 mole) of m-(diethylamino)acetophenone and 13.6 g. (0.184 mole) of ethyl formate in 200 ml. ethyl ether, keeping the temperature below 5°. After the addition is complete, the mixture is allowed to stir at room temperature overnight.

200 ml. water is then added and the aqueous phase separated. The ethyl ether phase is extracted with an additional 150 ml. of water, and the combined aqueous extracts brought to pH 9.2 with acetic acid. Cyanoacetamide (23.2 g., 0.276 mole) is added, and the solution kept at 90° for 6 hours. After standing at room temperature overnight, the crude pyridone nitrile is collected on a filter. Recrystallization from ethanol/DMSO gives 16 g. of pure 6-[m-(diethylamino)-phenyl-1,2-dihydro-2-oxonicotinonitrile, m.p. 229°–232°.

r.
6-[p-(4-Methyl-1-piperazinyl)phenyl-1,2-dihydro-1-methyl-2-oxonicotinonitrile.

Sodium methoxide 95.5% (29 g.) is suspended in 250 ml. of tetrahydrofuran and stirred and cooled. 50 ml. of ethyl formate and 109 g. p-(4-methyl-1-piperazinyl)acetophenone are dissolved in tetrahydrofuran 600 ml., and this solution is added slowly to the above suspension holding the temperature about 11° C. The mixture is stirred overnight at room temperature and the solid product is separated by filtration, washed with tetrahydrofuran and then ether.

The above solid is immediately dissolved in 1 liter of water, 12 ml. piperidine, 6.4 ml. acetic acid and 49 g. of N-methylcyanoacetamide are then added. The pH is adjusted from 10 to 9.5 with a little acetic acid (2–3 ml.). The solution is refluxed a total of 3 hours (in two 1.5 hour periods with cooling between). The suspension is cooled and collected by filtration as a waxy solid (122 g.). This solid is triturated using powerful mechanical stirring with a sharp cutting blade in 500 ml. methylene chloride. The yellow solution is separated by decantation; dried over magnesium sulfate, filtered evaporated to dryness, dissolved in tetrahydrofuran. The semisolid is precipitated by two successive additions each of 1 liter of petroleum ether. The combined semisolid is triturated with 25 ml. tetrahydrofuran, the yellow solid filtered off and dried over $P_2O_5$ (high vacuum overnight) giving 1.69 g. An additional 2.11 g. is recovered by reworking the various ethylene chloride residues, the total 3.79 g. is dissolved in 180 ml. of 1-1 ethanol/tetrahydrofuran and filtered through a filteraid pad. The product, 6-[p-(4-methyl-1-piperazinyl)phenyl]-1,2-dihydro-1-methyl-2-oxonicotionitrile slowly crystallizes from the cooled filtrate, yield 2.35 g., m.p. 238°–42° dec.

s.
6-[3-Chloro-4-(4-methyl-1-piperazinyl)phenyl-1,2-dihydro-2-oxonicotinonitrile.

Sodium hydride 2.03 g. (0.0844 mole) is suspended in 200 ml. of benzene and to this suspension is added dropwise a solution in 60 ml. of benzene, 10.25 g. (0.0422 mole) of 3'-chloro-4'-(4-methyl-1-piperazinyl)acetophenone and 4 ml. of ethyl formate. After ¼ is added, a few drops of ethanol are added and the temperature is raised to 50° to initiate hydrogen evolution. The addition is completed at 50° and stirring is continued overnight at room temperature. Water (100 ml.) is added to the stirred suspension and the two layers are separated. The benzene layer is washed several times with about 50 ml. water each.

The combined water layers are adjusted to pH 9-9.1 with acetic acid and piperidine giving a clear solution. Cyanoacetamide 5.3 g. (50% excess) is introduced and the mixture is refluxed (95°) overnight. The precipitate of 6-[3-chloro-4-(4methyl-1-piperazinyl)phenyl-1,2-dihydro-2-oxonicotinonitrile is collected, washed with water and dried, giving 11.5 g. A 5 g. sample is further purified by dissolving in hot dilute acetic acid and precipitating at pH 6-7 by partially neutralizing with N alkali. 4.5 g. of material shown to be pure by thin layer chromotography is obtained $\lambda$ 369 E'' = 686 (methanol).

t. 6-(m-Nitrophenyl)-1,2-dihydro-2-oxonicotinonitrile

Sodium methylate 11.9 g. (0.22 mole, 10% excess) is suspended in 100 ml. of benzene. The suspension is cooled and a previously prepared solution of 20 ml. ethyl formate (0.25 mole, 25% excess) and m-nitroacetropenone 33 g. (0.2 mole) in 260 ml. benzene is added dropwise rapidly (20 minutes). The temperature is maintained at 8° + 2° by means of an ice bath. The suspension is stirred overnight and 800 ml. of water is added to the reaction mixture. Two layers form with a suspended solid. The solid is removed by filtration, the layers separated and to the aqueous filtrate is added 16.8 g. of 2-cyanoacetamide. The mixture, adjusted to pH 8.5-9, is refluxed overnight when the pH has dropped to 6.8 and a tan solid has precipitated. The product 6-(m-nitrophenyl)-1,2-dihydro-2-oxonicotinonitrile is collected, washed with water and dried at 60° in vacuo for 3 hours, yield 11.34 g., m.p. 306°–308° dec. $\lambda$ 355 $\mu$, E'' = 431 (methanol). Molecular ion M = 241.

u.
6-[m-(1-Pyrrolidinyl)phenyl]-1,2-dihydro-2-oxonicotinonitrile.

Sodium hydride 1,2 g. (0.05 mole) is suspended with stirring in 50 ml. of benzene and a solution of 4.7 g. of m-(1-pyrrolidinyl)acetophenone and 5 ml. of ethyl formate in 75 ml. of benzene is added to the suspension in a dropwise manner. After one quarter is added, 1 ml. of ethanol is added and the reaction mixture is heated to 40°. This temperature is maintained until all the reactants have been added. The stirring at room temperature is continued overnight. Next, water (50 ml.) is added and the layers are separated and the benzene layer washed several times with water. The combined aqueous solution is adjusted to pH 9-9.1 with acetic acid and 3.12 g. (50% excess) of 2-cyanoacetamide added to the solution and the mixture refluxed overnight. The precipitated solid is filtered off, washed with acetonitrile and hot ethanol and dried to give 6-[m-(1-pyrrolidinyl)phenyl]-1,2-dihydro-2-oxonicotinonitrile, yellow solid melting above 290°. $\lambda$ = 354 E'' = 482 (methanol)

v.
6-(m-Piperidinylphenyl)-1,2-dihydro-2-oxonicotinonitrile

A solution of 10.2 g. (0.05 mole) of m-piperidinylacetophenone and 7.1 ml. (0.075 mole) of ethyl formate in 50 ml. of ethyl ether is added to a stirred suspension of 5.4 g. (0.1 mole) of sodium methoxide in 250 ml. ethyl ether, keeping the temperature below 5°. Stirring is continued overnight at room temperature. Cold water is added to the mixture, the layers are separated and washed with water. The combined aqueous extract (300 ml.) is adjusted to pH 9-9.1, 6.3 g. of cyanoacetamide is added and the solution is refluxed for 4 hours (95°). The suspension is cooled and the product is filtered off, washed with 100 ml. water then 200 ml. acetonitrile. The bright yellow solid 6-(m-piperidinylphenyl)-1,2-dihydro-2-oxonicotinonitrile is dried, yielding 6.92 g. $\lambda$ = 355 E'' = 682 (methanol)

w.
6-[m-(Methylamino)phenyl]-1,2-dihydro-2-oxonicotinitrile.

A suspension of 3.1 g. (0.057 mole, a 10% excess) of sodium methoxide in 60 ml. ethyl ether, and under nitrogen is cooled in ice and is treated dropwise with a solution of 7.77 g. (0.052 mole) of m-(methylamino)-acetophenone and 4.25 ml. (0.052 mole) of ethyl formate in 60 ml. ethyl ether. Cooling is maintained throughout the addition. When the addition is complete, the cooling is discontinued and the suspension allowed to stir at room temperature overnight.

The suspension is treated with 60 ml. of water and the layer separated. The ethyl ether layer is washed with an additional 45 ml. of water. The combined aqueous phase is brought to pH 9.1 with acetic acid, and 6.6 g. (0.078 mole) of 2-cyanoacetamide added. The solution is kept at 90° for 6 hours, then cooled. The crude solid is collected and recrystallized from DMSO/water to give 4.1 g. of 6-[m-(methylamino)phenyl]-1,2-dihydro-2-oxonicotinonitrile as a yellow solid, m.p. 288°–290° d.

x.
6-[m-(Propylamino)phenyl]-1,2-dihydro-2-oxonicotinonitrile.

A suspension of 4.48 g. (0.083 mole, a 10% excess) of sodium methoxide in 100 ml. ethyl ether is cooled in ice and treated dropwise with a solution of 13.3 g. (0.075 mole) of m-(propylamino)acetophenone and 6.05 ml. (0.075 mole) of ethyl formate in 100 ml. ethyl ether under nitrogen. Cooling was maintained throughout the addition. When the addition is complete, the cooling is removed and the suspension allowed to stir at room temperature overnight.

The suspension is treated with 100 ml. water and the layers separated. The ethyl ether layer is washed with an additional 50 ml. water. The combined aqueous layers are brought to pH 9 with acetic acid with treated with 9.51 g. (0.11 mole) of 2-cyanoacetamide. The solution is kept at 90° for 6 hours, then cooled. The crude precipitated product is collected and dried. Recrystallization from DMSO/water gives 6.1 g. of 6-[m-(propylamino)phenyl]-1,2-dihydro-2-oxonicotinonitrile. as a yellow-brown solid, m.p. 215°–220° d.

C.
6-SUBSTITUTED-1,2-DIHYDRO-2-OXONICOTINIC ACIDS.

a.
6-[p-(4-Methyl-1-piperazinyl)phenyl]-1,2-dihydro-2-oxonicotinic Acid.

A mixture of 457 g. of 6-[p-(4-methyl-1-piperazinyl)-phenyl]-1,2-dihydro-2-oxonicotinonitrile and 4570 g. of 20% aqueous potassium hydroxide is heated at 105° in an agitated stainless steel autoclave for 40 hours, then poured into a mixture of 1.4 kg. of ice and 1.4 liters of concentrated hydrochloric acid. The pH of the resulting mixture is adjusted to pH 6.5 with 5% aqueous sodium hydroxide and the precipitate of 6-[p-(4-methyl-1-piperazinyl)phenyl]-1,2-dihydro-2-oxonicotinic acid is collected by filtration, washed with water, then with 95% ethanol, and dried; m.p. 300° (dec.).

In a similar manner the following acids are prepared by hydrolysis of the corresponding nitrile with ten times its weight of 20% aqueous potassium hydroxide, followed by acidification and suitable adjustment of the pH.

b. 6-[p-(Dimethylamino)phenyl]-1,2-dihydro-2-oxonicotinic Acid.
c. 6-[m-(Dimethylamino)phenyl]-1,2-dihydro-2-oxonicotinic Acid [m.p. 275°–280° (dec.) after crystallization from aqueous dimethyl sulfoxide.]
d. 6-[p-(4-Propyl-1-piperazinyl)phenyl]-1,2-dihydro-2-oxonicotinic Acid [m.p. 268°–269° (dec.).]
e. 6-(p-Piperidinophenyl)-1,2-dihydro-2-oxonicotinic Acid.
f. 6-(p-Morpholinophenyl)-1,2-dihydro-2-oxonicotinic Acid [m.p. >300° (dec.).]
g. 6-[p-(4-Piperidinopiperidino)phenyl]-1,2-dihydro-2-oxonicotinic Acid.
h. 6-[p-(4-Cyclohexyl-1-piperazinyl)phenyl]-1,2-dihydro-2-oxonicotinic Acid [m.p. 300°–305° (dec.).]
i. 6-[p-(4-Benzyl-1-piperazinyl)phenyl]-1,2-dihydro-2-oxonicotinic Acid [m.p. 276°–280° (dec.).
j. 6-[p-(4-Ethyl-1-piperazinyl)phenyl]-1,2-dihydro-2-oxonicotinic Acid [m.p. 295°–296°.]
k. 6-[p-[4-(m-Chlorophenyl)-1-piperazinyl]phenyl]-1,2-dihydro-2-oxonicotinic Acid.
l. 6-[p-(4-Phenyl-1-piperazinyl)phenyl]-1,2-dihydro-2-oxonicotinic Acid.
m. 6-[p-[4-(1-Pyrrolidinyl)piperidino]phenyl]-1,2-dihydro-2-oxonicotinic Acid.
n. 6-[p-(Hexahydro-4-methyl-1H-1,4-diazepin-1-yl)phenyl]-1,2-dihydro-2-oxonicotinic Acid.
o. 6-[p-(4-Methyl-1-piperazinyl)phenyl]-1,4-dihydro-1-methyl-2-oxonicotinic Acid.
p. 6-[o-(4-Methyl-1-piperazinyl)phenyl]-1,2-dihydro-2-oxonicotinic Acid.

A mixture of 14.7 g. of 6-[o-(4-Methyl-1-piperazinyl)-phenyl]-1,2-dihydro-2-oxonicotinonitrile and 246 ml. of 17% aqueous sodium hydroxide is stirred and heated at reflux 43 hours, then filtered hot. The filtrate is poured into a solution of 63 ml. of concentrated hydrochloric acid in 350 ml. of ice water. The resulting precipitate of 6-[o-(4-methyl-1-piperazinyl)phenyl]-1,2-dihydro-2-oxonicotinic acid is collected by filtration, washed with water and dried; m.p. 241.5°–215.5° (dec.) after crystallization from toluene-cyclohexane.

q. 6-[m-(4-Methyl-1-piperazinyl)phenyl]-1,2-dihydro-2-oxonicotinic Acid.

A stainless steel autoclave is charged with 14.8 g. of 6-[m-(4-methyl-1-piperazinyl)phenyl]-1,2-dihydro-2-nicotinonitrile and a solution of 30 g. potassium hydroxide in 120 ml. water is added. The mixture is heated at 105° for 41 hours, then poured over ice and hydrochloric acid. The pH is adjusted to 6.4 and 15.6 g. (89%) of 6-[m-(4-methyl-1-piperazinyl)phenyl]-1,2-dihydro-2-oxonicotinic acid hydrochloride is collected as a yellow solid, m.p. 209°–310° d.

r.
6-[m-(Diethylamino)phenyl]-1,2-dihydro-2-oxonicotinic Acid.

A stainless steel autoclave is charged with 15.4 g. (0.0577 mole) of 6-[m-(diethylamino)phenyl]-1,2- dihydro-2-oxonicotinonitrile, and a solution of 30 g. KOH in 120 ml. water is added. The mixture was heated at 105° for 41 hours, then poured onto ice + conc HCl. The pH was adjusted to 6.4 and the precipitated product collected. Recrystallization from DMSO/water gave 15.4 g. (93.4%) of pure 6-[m-(diethylamino)phenyl]-1,2-dihydro-2-oxonicotinic acid, m.p. 256°–258° d.

s. 6-[p-(4-Methyl-1-piperazinyl)phenyl]-1,2-dihydro-1-methyl-2-oxonicotinic Acid.

6-[p-(4-Methyl-1-piperazinyl)phenyl]-1,2-dihydro-1-methyl-2-oxonicotinonitrile 2 g., is heated 40 hours at 105° in 16 ml. water containing 4 g. potassium hydroxide. Hydrolysis is incomplete. The recovered partially hydrolyzed material (1.74 g., m.p. 291°-30°) is treated in a pressure vessel in 4 ml. water, 12 ml. ethylene glycol and 4 g., potassium hydroxide at 170° for 38 hours. The reaction mixture is poured into 6.5 ml. concentrated hydrochloric acid and 7 g. ice. The slightly turbid solution is filtered and the filtrate is brought to dryness in a steam bath using a rotatory evaporator under vacuum. The residue is mixed with 12 ml. cold water (pH about 3.3) and filtered. The filtrate layer deposits additional solid which is also filtered off and combined to give a total of 0.58 g. of 6-[p-(4-methyl-1-piperazinyl)phenyl]-1,2-dihydro-1-methyl-2-oxonicotinic acid after drying over phosphorus pentoxide in vacuo.

t. 6-[3-Chloro-4-(4-methyl-1-piperazinyl)phenyl]-1,2-dihydro-2-oxonicotinic Acid.

6-[3-Chloro-4-(4-methyl-1-piperazinyl)phenyl]-1,2-dihydro-2-oxonicotinonitrile 3.3 g. is heated under pressure at 105° in about 25 ml. 20% potassium hydroxide for 40 hours. The acidified solution (pH 5-7) is filtered, the collected precipitate is dissolved in diluted hydrochloric acid (< 10%) and again precipitated by bringing to pH 5-7.5 with 1N sodium hydroxide. The precipitate of 6-[3-chloro-4-(4-methyl-1-piperazinyl)phenyl]-1,2-dihydro-2-oxonicotinic acid is collected and crystallized from DMSO plus tetrahydrofuran/CH$_3$CN 1—1. giving 1.8 g. λ 329 mμ E" = 596 (methanol)

u. 6-[3-Bromo-4-(4-methyl-1-piperazinyl)phenyl]-4(or 5)-bromo-1,2-dihydro-2-oxonicotinic Acid.

6-[p-(4-methyl-1-piperazinyl)phenyl]-1,2-dihydro-2-oxonicotinic acid 3.13 g. (0.01 mole) is dissolved in 100 ml. of 2N sulfuric acid with the aid of stirring at room temperature. Bromine 3.2 g. (1.1 ml., 0.02 mole) is added to the solution in a dropwise manner causing a solid to precipitate. The suspension is stirred for 1 hour and filtered. The fine yellow precipitate is washed with ethanol and dissolved in water by addition of sodium hydroxide (pH = 12). The basic solution is filtered to remove insoluble solid and the filtrate is acidified with 2N sulfuric to pH 5.5-6.0. The product 6-[3-bromo-4-(4-methyl-1-piperazinyl)phenyl]-4(or 5)-bromo-1,2-dihydro-2-oxonicotinic acid precipitates and is collected by filtration, washed with water and dried.

v. 6-(m-Nitrophenyl)-1,2-dihydro-2-oxonicotinic Acid.

A suspension of 147 g. (0.608 mole) of 6-(m-nitrophenyl)-1,2-dihydro-2-oxonicotinonitrile in 3.7 liter of 5% potassium hydroxide is heated on the steam bath for 46 hours (solution complete before 42 hours). The solution is heavily charcoaled twice, and the filtrate is poured into approximately 2 kg. ice containing 250 ml. concentrated hydrochloric acid. The yellowish precipitate is collected by filtration and washed twice with water and twice with methanol, finally with ethyl ether giving 69.8 g. (60.6%) after drying in vacuo for 72 hours. The product 6-(m-nitrophenyl)-1,2-dihydro-2-oxonicotinic acid is further crystallized from glacial acetic acid with charcoal, washed with acetic acid then ethyl ether, m.p. 303°-304°.

w. 6-[m-(1-Pyrollidinyl)phenyl]-1,2-dihydro-2-oxonicotinic Acid.

6-[m-(1-Pyrollidinyl)phenyl]-1,2-dihydro-2-oxonicotinonitrile (2.08 g.) is heated under pressure at 105° in 20 ml. of 20% potassium hydroxide for 40 hours. The reaction mixture is poured into 6.5 ml. concentrated hydrochloric acid and 10 g. ice. The product, 6-[m-(1-pyrrolidinyl)phenyl]-1,2-dihydro-2-oxonicotinic acid is collected by filtration, 1.9 g. λ = 326 mμ E" = 470 (in pH 7 buffer)

x. 6-(m-Piperidinylphenyl)-1,2-dihydro-2-oxonicotinic Acid.

6-(m-Piperidinylphenyl)-1,2-dihydro-2-oxonicotinonitrile (5.6 g., 20 mmoles) is dissolved in 300 ml. 6% potassium hydroxide in a stainless steel container and heated on the steambath over the weekend. The heating is changed to a Glascol mantle and the solution is refluxed (100°) for an additional 3 hours. The solution is poured into 200 ml. ice-water mixture and acidified to about pH 3 with hydrochloric acid. The collected solid 6-(m-piperidinylphenyl)-1,2-dihydro-2-oxonicotinic acid is washed with water then acetonitrile (250 ml.) giving yield of light yellow solid, 5.35 g. λ = 324 E" = 482 (in pH 7 buffer)

y. 6-[m-(Methylamino)phenyl]-1,2-dihydro-2-oxonicotinic Acid.

A stainless steel autoclave is charged with 4.03 of 6-[m-(methylamino)phenyl]-1,2-dihydro-2-oxonicotinonitrile, and a solution of 8.0 g. potassium hydroxide in 32 ml. water is added. After keeping at 105° for 41 hours, the solution is poured onto ice and hydrochloric acid. The pH is adjusted to 6.4 with dilute sodium hydroxide. After stirring for 1 hour, there is collected 4.04 g. of the crude acid. Recrystallization from DMSO/water gives 3.83 g. of 6-[m-(methylamino)phenyl]-1,2-dihydro-2-oxonicotinic acid as a yellow solid, m.p. 283°-284° d.

z. 6-[m-(propylamino)phenyl]-1,2-dihydro-2-oxonicotinic Acid.

A stainless steel autoclave is charged with 5.92 g. of 6-[m-(propylamino)phenyl]-1,2-dihydro-2-oxonicotinonitrile, and a solution of 13 g. potassium hydroxide in 48 ml. water is added. The solution is kept at 105° for 40 hours, and then poured onto ice and hydrochloric acid. The pH is adjusted to 6.3 with dilute sodium hydroxide, and the suspension stirred for 1 hour. The crude acid is collected and dried. Recrystallization from DMSO/water gives 3.8 g. of 6-[m-(propylamino)-phenyl]-1,2-dihydro-2-oxonicotinic acid as a greenish-brown solid, m.p. 251°-54° d.

D. 6-SUBSTITUTED-1,2-DIHYDRO-2-OXONICOTINYL CHLORIDE HYDROCHLORIDES.

a. 6-[p-(4-Methyl-1-piperazinyl)phenyl]-1,2-dihydro-2-oxonicotinyl Chloride Hydrochloride.

A mixture of 100 g. of finely divided 6-[p-(4-methyl-1-piperazinyl)phenyl]-1,2-dihydro-2-oxonicotinic acid and 1.0 liter of thionyl chloride is stirred at room temperature for 16 hours, then diluted with 1.0 liter of dichloromethane. The resulting precipitate of 6-[p-(4-methyl-1-piperazinyl)phenyl]-1,2-dihydro-2-oxonicotinyl chloride hydrochloride is collected by filtration, washed with dichloromethane and dried.

In a similar manner, the following acid chloride hydrochlorides are prepared by reaction of the corresponding acid with thionyl chloride.

b. 6-[p-(Dimethylamino)phenyl]-1,2-dihydro-2-oxonicotinyl Chloride Hydrochloride c. 6-[m-(Dimethylamino)phenyl]-1,2-dihydro-2-oxonicotinyl Chloride Hydrochloride.

d. 6-[p-(4-Propyl-1-piperazinyl)phenyl]-1,2-dihydro-2-oxonicotinyl Chloride Hydrochloride.

e. 6-(p-Piperidinophenyl)-1,2-dihydro-2-oxonicotinyl Chloride Hydrochloride.

f. 6-[p-(4-Piperidinopiperidino)phenyl]-1,2-dihydro-2--oxonicotinyl Chloride Hydrochloride.

g. 6-[p-(4-Cyclohexyl-1-piperazinyl)phenyl]-1,2-dihydro--2-oxonicotinyl Chloride Hydrochloride.

h. 6-[p-4-Benzyl-1-piperazinyl)phenyl]-1,2-dihydro-2--oxonicotinyl Chloride Hydrochloride.

i. 6-[p-(4-Ethyl-1-piperazinyl)phenyl]-1,2-dihydro-2--oxonicotinyl Chloride Hydrochloride.

j. 6-[p-[4-(m-Chlorophenyl)-1-piperazinyl]phenyl]-1,-2--dihydro-2-oxonicotinyl Chloride Hydrochloride.

k. 6-[p-(4-Phenyl-1-piperazinyl)phenyl]-1,2-dihydro--2--oxonicotinyl Chloride Hydrochloride. p1 l. 6-[p-[4-(1-Pyrrolidinyl)piperidino]phenyl]-1,2---dihydro-2-oxonicotinyl Chloride Hydrochloride.

m. 6-[p-(Hexahydro-4-methyl-1H-1,4-diazepin-1-yl)p-henyl]--1,2-dihydro-2-oxonicotinyl Chloride Hydrochloride.

n. 6-[p-(4-Methyl-1-piperazinyl)phenyl]-1,2-dihydro--1--methyl-2-oxonicotinyl Chloride Hydrochloride.

o. 6-[o-(4-Pentyl-1-piperazinyl)phenyl]-1,2-dihydro-2-oxonicotinyl Chloride Hydrochloride.

A mixture of 3.44 g. of finely divided 6-[o-(4-methyl-1-piperazinyl)phenyl]-1,2-dihydro-2-oxonicotinic acid and 35 ml. of thionyl chloride is stirred at room temperature for 16 hours, then diluted with 150 ml. of dichloromethane. The resulting solution is evaporated at reduced pressure and the resulting precipitate of 6-[o-(4-methyl-1-piperazinyl)phenyl]-1,2-dihydro-2-oxonicotinyl chloride hydrochloride is collected by filtration, washed with dichloromethane and dried.

p.
6-[m-(4-Methyl-1-piperazinyl)phenyl]-1,2-dihydro-2-oxonicotinyl Chloride Hydrochloride.

6-[m-(4-Methyl-1-piperazinyl)phenyl]-1,2-dihydro-2-oxonicotinic acid hydrochloride (1.5 g.) is added to 75 ml. $SOCl_2$ containing 20 drops of N,N-dimethyl-formamide. The material appears to be partially soluble and after a few minutes a new solid starts to appear. The suspension is stirred at room temperature overnight. Dichloromethane is then added and the pale yellow solid collected and washed with dichloromethane. There is obtained 1.44 g. of 6[m-(4-methyl-1-piperazinyl)-phenyl]-1,2-dihydro-2-oxonicotinyl chloride hydrochloride.

q.
6-[m-(Diethylamino)phenyl]-1,2-dihydro-2-oxonicotinyl Chloride Hydrochloride.

A suspension of 3.0 g. (10.48 mmoles) of 6-[m-(diethylamino)phenyl]-1,2-dihydro-2-oxonicotinic acid in 50 ml. dichloromethane under nitrogen is treated with 0.85 ml. (11.54 mmoles)of thionyl chloride. Solution occurred at once and in about 15 minutes a solid started to appear. The suspension is allowed to stire at room temperature overnight. The solid 6-[m-(diethylamino)-phenyl]-1,2-dihydro-2-oxonicotinyl chloride, hydrochloride is collected and washed with dichloromethane. There is obtained 3.28 g. of the acid chloride, hydrochloride.

r.
6-[p-(4-Methyl-1-piperazinyl)phenyl]-1,2-dihydro-1-methyl-2-oxonicotinyl Chloride Hydrochloride.

6-[p-(4-Methyl-1-piperazinyl)phenyl]-1,2-dihydro-1-methyl-2-oxonicotinic acid 0.5 g. is added to 5 ml. of thionyl chloride. The solid dissolves quickly with effervescence and the resulting solution is stirred 3 hours. The product is precipitated by adding 10 volumes hexane, and the solid 6-[p-(4-methyl-1-piperazinyl)-phenyl]-1,2-dihydro-1-methyl-2-oxonicotinyl chloride hydrochloride separated by decantation. Washing with hexane by decantation is repeated several times and the product finally is suspended in tetrahydrofuran and used as a suspension in the preparation of the compounds of this invention.

s.
6-[3-Chloro-4-(4-methyl-1-piperazinyl)phenyl]-1,2-dihydro-2-oxonicotinyl Chloride Hydrochloride.

6-[3-Chloro-4-(4-methyl-1-piperazinyl)phenyl]-1,2-dihydro-2-oxonicotinic acid 1.73 g. (0.005 mole) is added to thionyl chloride, 50 ml. with mechanical stirring. The mixture is stirred overnight (maximum temperature about 28°. A large volume of hexane is added and the product 6-[3-chloro-4-(4-methyl-1-piperazinyl)-phenyl]-1,2-dihydro-2-oxonicotinyl chloride hydrochloride collected by filtration and dried over phosphorus pentoxide at high vacuum. The product is used immediately in the preparation of compounds of the invention.

t. 6-[3-Bromo-4-(4-methyl-1-piperazinyl)phenyl]-4(or 5)-bromo-1,2-dihydro-2-oxonicotinyl Chloride Hydrochloride.

6-[3-Bromo-4-(4-methyl-1-piperazinyl)phenyl]-4(or 5)-bromo-1,2-dihydro-2-oxonicotinic acid 2.36 g. is added to 25 ml. of thionyl chloride and the mixture is allowed to stir at room temperature overnight. The solution is filtered from a trace of solid and the product is precipitated by adding hexane (large volume). The gum solidifies on standing and is filtered off and dried over phosphorus pentoxide to give 6-[3-bromo-4-(4-methyl-1-piperazinyl)phenyl]-4(or 5)-bromo-1,2-dihydro-2-oxonicotinyl chloride hydrochloride.

u. 6-(m-Nitrophenyl)-1,2-dihydro-2-oxonicotinyl Chloride.

A 5 g. sample of 6-(m-nitrophenyl)-1,2-dihydro-2-oxonicotinic acid is suspended in 100 ml. thionyl chloride and stirred at room temperature overnight. The product 6-(m-nitrophenyl)-1,2-dihydro-2-oxonicotinyl chloride is carefully filtered off and washed with hexane and used directly in the preparation of compounds of the present invention.

v.

6-[m-(1-Pyrrolidinyl)phenyl]-1,2-dihydro-2-oxonicotinyl Chloride Hydrochloride.

The 6-[m-(1-Pyrrolidinyl)phenyl]-1,2-dihydro-2-oxonicotinic acid (1.9 g.) is suspended in 40 ml. thionyl chloride and stirred at room temperature for 4 hours. A trace of undissolved solid is removed by filtration and the filtrate is diluted with 500 ml. of hexane. A gum which forms at first changes to a tan solid on continued stirring. The solid 6-[m-(1-pyrroli-dinyl)phenyl]-1,2-dihydro-2-oxonicotinyl chloride hydrochloride is collected quickly by filtration and dried over phosphorus pentoxide overnight in vacuo. The 1.8 g. of product so obtained is taken on the the next step without further purification.

w. 6-(m-Piperidinylphenyl)-1,2-dihydro-2-oxonicotinyl Chloride Hydrochloride.

6-(m-Piperidinylphenyl)-1,2-dihydro-2-oxonicotinic acid, 5.22 g. (0.0165 mole) is added to 100 ml. of thionyl chloride and the mixture is stirred overnight at room temperature. The solid 6-(m-piperidinylphenyl)-1,2-dihydro-2-oxonicotinyl chloride hydrochloride is separated by filtration, washed three times with 100 ml. of hexane and dried over phosphorous pentoxide in vacuo. The product may be used directly in the next step.

x. 6-[m-(Methylamino)phenyl]1,2-dihydro-2-oxonicotinyl Chloride Hydrochloride.

6-[m-(Methylamino)phenyl]-1,2-dihydro-2-oxonicotinic acid (1.0 g.) is added to 10 ml. of $SOCl_2$ containing 10 drops of dimethylformamide. Solution soon occurred, and after about 15 minutes, a new solid starts to appear. The mixture is diluted with methylene chloride, and the 6-[m-(methylamino)phenyl]1,2-dihydro-2-oxonicotinyl chloride hydrochloride collected and washed with methylene chloride.

y. 6-[m-(Propylamino)phenyl]-1,2-dihydro-2-oxonicotinyl Chloride Hydrochloride.

6-[m-(Propylamino)phenyl]-1,2-dihydro-2-oxonicotinic acid (1.0 g.) is added to 10 ml. thionyl chloride containing 10 drops of dimethylformamide. Solution soon occurs and after a half hour a new solid appears. The mixture is diluted with methylene chloride and the 6[-m-(propylamino)phenyl]-1,2-dihydro-2-oxonicotinyl chloride hydrochloride collected and washed with methylene chloride.

z. 6-[o-(4-Methyl-1-piperazinyl)phenyl]-1,2-dihydro-2-oxonicotinyl Chloride Hydrochloride].

A mixture of 3.44 g. of finely divided 6-[o--(4-methyl-1-piperazinyl)phenyl]-1,2-dihydro-2-oxonicotinic acid and 35 ml. of thionly chloride is stirred at room temperature for 16 hours, then diluted with 150 ml. of dichloromethane. The resulting solution is evaporated at reduced pressure and the resulting precipitate of 6-[o-(4-methyl-1-piperazinyl)phenyl]-1,2-dihydro-2-oxonicotinyl chloride hydrochloride is collected by filtration, washed with dichloromethane and dried.

E. D-N-(TRIMETHYLSILYL)-2-PHENYLGLYCINE, TRIMETHYLSILYL ESTER.

A mixture of 16.6 g. of D-(-)-2-phenylglycine, 30 ml. of trimethylsilyl chloride and 35 ml. of triethylamine in 1.0 liter of dichloromethane is stirred for 1 hour at reduced pressure, resulting in a solution containing D-N-(trimethylsilyl)-2-phenylglycine, trimethylsilyl ester.

F. D-(+)-N-[6-[p-(4-METHYL-1-PIPERAZINYL)-PHENYL]-1,2-DIHYDRO-2-OXONICOTINYL]-2-PHENYLGLYCINE.

The above solution containing D-N-(trimethylsilyl)-phenylglycine, is cooled to 5° and 24.8 g. of N-[6-[p-(4-methyl-1-piperazinyl)phenyl]-1,2-dihydro-2-oxonicotinyl chloride hydrochloride is added in portions with vigorous stirring. A solution of 35 ml. of triethylamine in 50 ml. of dichloromethane is then added dropwise with stirring over a period of 1 hour. The resulting mixture is allowed to stand at room temperature for 3 hours, then diluted with 5 ml. of water in 100 ml. of dimethylformamide. The resulting mixture contains D-(+)-N-[6-[p-(4-methyl-1-piperazinyl)phenyl]-1,2-dihydro-2-oxonicotinyl]-2-phenylglycine.

[The D-(+)-N-[6-[p-(4-methyl-1-piperazinyl)-phenyl]-1,2-dihydro-2-oxonicotinyl]-2-phenylglycine may be isolated, if desired, by dilution of the reaction mixture with water and isolating the product by filtration; m.p. 212°–215° (dec.), $[\alpha]_d^{25} + 101°$ (1.08% in 3:1 dimethylformamide-pyridine)]

G. MISCELLANEOUS INTERMEDIATES a. 3-[[(5-Methyl-1,3,4-thiadiazol-2-yl)thio]methyl]-7-(D-α-amino-α-phenylacetamido)-3-cephem-4-carboxylic Acid.

A solution of 10.0 g. (0.024 mole) of cephalothin, sodium salt, 2.01 g. (0.024 mole) of sodium bicarbonate, and 3.87 g. (0.029 mole) of 2-methyl-5-mercapto-1,3,4-thiadiazole in 250 ml. of phosphate buffer (pH 6.4) is heated at 60° for 5.5 hours. The solution is cooled and acidified to pH 2.0 causing a gum to form. The gum is dissolved in acetone/ethyl acetate and filtered to remove some insoluble material. Addition of ethyl ether to the filtrate precipitated 4.75 g. of the product, 3-[[(5-methyl-1,3,4-thiadiazol-2-yl)thio]methyl]-7-[(2-thienyl)-acetamido]-3-cephem-4-carboxylic acid $[\alpha]_D^{25} -44°$ (c = 1.0% in methanol). Addition of hexane to the filtrate caused an additional 1.75 g. of product to precipitate, $[\alpha]_D^{25} -36°$ (c = 1.0% in methanol).

The above produced carboxylic acid 3.35 g. (7.14 mmoles), N,N-dimethylaniline 2.9 ml. (22.85 mmoles) and dimethyldichlorosilane 1.47 ml. (12.14 mmoles) is added to methylene chloride (100 ml.), and the mixture allowed to stir at room temperature for 2.5 hours.

The mixture is cooled to −54° and phosphorous pentachloride is 1.61 g. (7.71 mmoles) added, and the mixture stirred at −40° for 2 hours. After recooling to −54° and adding 0.36 ml. (2.86 mmoles) of N,N-dimethylaniline followed by 14.4 ml. (0.192 mmole) of 1-propanol, the mixture is stirred at −40° for 2.5 hours. Next, water 120 ml. and methanol 40 ml. are added and adjust the pH to 3.5 with ammonium bicarbonate. After standing in a refrigerator overnight, filter to collect solid 3-[[(5-methyl-1,3,4-thiadiazol-2-yl)thio]methyl]-7-amino-3-cephem-4-carboxylic acid formed (2.1 g.).

A suspension of 1.0 g. (2.9 mmoles) of the above prepared thiophene derivative in 20 ml. tetrahydrofuran is cooled in ice and treated with 0.73 ml. (5.8 mmoles) of trimethylsilyl chloride followed by 0.81 ml. (5.8 mmoles) of triethylamine. The mixture is allowed to stir at room temperature for 1 hour, and is then recooled in ice.

In a separate flask, 0.87 g. (2.9 mmoles) of the potassium salt of N-[1-methyl-2-(ethoxycarbonyl)vinyl]-D-α-aminophenylacetic acid [Ber., 98, 792 (1965)] in 20 ml. tetrahydrofuran is treated with 0.35 g. (2.9 mmoles) of pivaloyl chloride in 10 ml. tetrahydrofuran. The mixture is allowed to stir at 0° for 10 minutes.

The above two reaction mixtures are combined, 0.41 ml. (2.9 mmoles) of triethylamine added and the mixture allowed to stir at 0° for one half hour, then at room temperature overnight.

Insoluble material is filtered off and the solvent removed under reduced pressure. The residue is taken up in 20 ml. of 3% sodium bicarbonate and the pH adjusted to 2.3 causing a gum to form, which is allowed to stir at room temperature for 1 hour. The mixture is filtered, and the filtrate extracted with ethyl ether. After adjusting the aqueous phase to pH 5.0, the solvent is removed under reduced pressure. The residue is taken up in dimethylacetamide and 1.0 ml. of sodium 2-ethylhexanoate (50% in n-butanol) added. After stirring for one half hour, the mixture is filtered to remove insoluble material. Upon the addition of ethyl ether/ethyl acetate to the filtrate, the sodium salt of 3-[[(5-methyl-1,3,4-thiadiazol-2-yl)thio]methyl]-7-(D-α-amino-α-phenylacetamido)-3-cephem-4-carboxylic acid precipitates in the form of a tan solid (650 mg.), $[\alpha]_D^{25} -28.6°$ ($c = 1.03\%$ in 75% dimethylformamide/25% pyridine).

b.
3-[[(2-Pyrimidinyl)thio]methyl]-7-(D-α-amino-α-phenylacetamido)-3-cephem-4-carboxylic Acid.

Cephalothin, sodium salt 10.0 g. (23.9 mmoles) sodium bicarbonate 2.01 g. (23.9 mmoles) and 2-mercaptopyrimidine 3.29 g. (29.3 mmoles) are added to a phosphate buffer (pH 6.4) 250 ml. and the mixture heated at 60° for 5.5 hours. After cooling and adjusting the pH to 3.4 with dilute hydrochloric acid, 3-[[(2-pyrimidinyl)-thio]-methyl]-7-[(2-thienyl)acetamido]-3-cephem-4-carboxylic acid precipitates and is collected and dried. 8.24 g.; $[\alpha]_D^{25} -105°$ ($c = 1.02\%$ in 75% dimethylformamide/25% pyridine).

The above prepared compound 7.99 g. (17.8 mmoles), N,N-dimethylaniline, 7.23 ml. (56.99 mmoles), and dimethyldichlorosilane, 3.65 ml. (30.28 mmoles) are added to methylene chloride (250 ml.), and the mixture allowed to stir at room temperature for 2.5 hours. The reaction mixture is cooled to −54° and 4.01 g. (19.24 mmoles) of phosphorus pentachloride added and the mixture stirred at −40° for 2 hours. The mixture is recooled to −54°, and 0.9 ml. (7.12 mmoles) of N,N-dimethylaniline added followed by 3.9 ml. (0.48 mole) of propanol, and the mixture allowed to stir at −40° for 2.5 hours. Water, 200 ml. and methanol 70 ml. is then added and the pH adjusted to 3.5 with ammonium bicarbonate. After standing at 0° overnight, 3-[[(2-pyrinidinyl)thio]methyl]-7-amino-3-cephem-4-carboxylic acid is filtered off, 4.74 g. $[\alpha]_D^{25} -150°$ ($c = 1.01\%$ in DMSO).

A suspension of 2.5 g. (7.73 mmoles) of the above prepared compound in 60 ml. tetrahydrofuran is cooled in ice and treated with 1.95 ml. (15.46 mmoles) of trimethylsilyl chloride followed by 2.17 ml. (15.46 mmoles) of triethylamine. The mixture is then allowed to stir at room temperature for 1 hour, and is then recooled in ice.

In a separate flask a solution of 2.33 g. (7.73 mmoles) of the potassium salt of N-[1-methyl-2-(ethoxycarbonyl)vinyl]-D-α-aminophenylacetic acid, 50 ml. tetrahydrofuran (heat to effect solution, then recool) is cooled in ice and 0.93 g. (7.73 mmoles) of pivaloyl chloride in 25 ml. tetrahydrofuran added. The mixture is stirred at 0° for 10 minutes.

The above two solutions are combined, 1.08 ml. (7.73 mmoles) of triethylamine added, and the new solution allowed to stir at 0° for ½ hour, then at room temperature overnight. Insoluble material is filtered off and the filtrate concentrated under reduced pressure. The residue was taken up in 50 ml. of 3% sodium bicarbonate solution and the pH adjusted to 2.3 with dilute hydrochloric acid causing a gummy solid to separate. The mixture is stirred at room temperature for 1 hour. The insoluble material is filtered off and the filtrate extracted with ethyl ether. The pH is adjusted to 5.0 and the water removed under reduced pressure at room temperature. The residue is taken up in dimethylacetamide and 2.0 ml. of sodium 2-ethylexanoate (50% in n-butanol) added. After filtering off some insoluble material, addition of ethyl ether/ethyl acetate to the filtrate precipitates the sodium salt of 3-[[(2-pyrimidinyl)thio]methyl]-7-(D-α-amino-α-phenylacetamido)-3-cephem-4-carboxylic acid. There is collected 1.37 g. of a tan solid, $[\alpha]_D^{25} -60°$ ($c = 1.0\%$ in 75% dimethylformamide/25% pyridine).

c.
3-(1-Benzoylthiomethyl)-7-[D-α-[6-[p-(4-methyl-1-piperazinyl)phenyl-1,2-dihydro-2-oxonicotinamido]-α-phenylacetamido]-3-cephem-4-carboxylic Acid.

A solution of 21.1 gm. of sodium cephalothin in 250 ml. of water containing 8.33 gm. of monobasic sodium phosphate, monohydrate, is treated with a solution of 10.6 gm. of sodium thiobenzoate in 15 ml. of water. The resulting mixture is heated to 90° C. over 15 minutes and held at 90° C. for 1 hour, with vigorous stirring. The mixture is cooled, filtered, and the precipitate is dissolved in 1300 ml. of aqueous acetone (1:1) at 40° C. The addition of 17.5 ml. of concentrated hydrochloric acid precipitates the thiobenzoate, $[\alpha]_D^{25} = -131°$ (1.04% in dioxane).

A stirred mixture, prepared from 500 ml. of dichloromethane, 21.3 gm. of the above prepared thiobenzoate, 17.25 ml. of N,N-dimethylaniline, and 9.3 ml. of chlorotrimethylsilane, is kept at ambient temperature for 2.5 hours, then cooled to −55°, and 10.3 gm. of phosphorus pentachloride added. After 2 hours at −40°, the mixture is cooled to −60° C., and 2.25 ml. of N,N-dimethylaniline is added, followed by 96 ml. of 1-propanol. The result is stirred at −40° C. for 2.5 hours, then cooled to −55° C. and treated with 750 ml. of ice-cold aqueous methanol (2:1). The mixture is warmed to 18° C., and brought to pH 3.5 by the addition of solid ammonium bicarbonate. The precipitate is collected, washed with dichloromethane, and with water, and dried, providing the deacylated product, $[\alpha]_D^{25} = -173°$ (0.275% in dimethylformanide).

A mixture of 2.04 gm. of the above prepared deacylated product in 60 ml. of chloroform is treated with 3.05 ml. of triethylamine and 2.25 ml. of chlorotrimethylsilane, stirred for 1 hour at room temperature, and cooled to 0° C. Triethylamine (0.8 ml.) is added, followed by a solution prepared by allowing 1.74 gm. of the potassium salt of N-[1-methyl-2-(ethoxycarbonyl)vinyl]-D-α-aminophenylacetic acid to react with 0.72 gm. of pivaloyl chloride in 50 ml. of tetrahydrofuran for 10 minutes at 0° C. The result is stirred for 40 minutes at 0°-5°, then overnight at ambient temperature. The mixture is filtered and evaporated to a heavy syrup which is stirred with 3% sodium bicarbonate, producing the N-[1-methyl-2-(ethoxycarbonyl)vinyl]-D-α-aminophenylacetyl derivative (dihydrate). This salt is suspended in water and the pH adjusted to 2.0 by addition of dilute hydrochloric acid, and the α-amino-α-phenylacetyl derivative precipitated and is collected, and dried.

Chlorotrimethylsilane (1.70 ml.) is added to an ice-cold solution of 2.62 gm. of the above prepared α-amino-α-phenylacetyl derivative in 80 ml. of dry N,N-dimethyl acetamide and 1.88 ml. of triethylamine. The mixture is stirred for 70 minutes at room temperature, re-cooled to 5° C., and treated with 2.0 gm. of 6-[p-(4-methyl-1-piperazinyl)phenyl]-1,2-dihydro-2-oxonicotinyl chloride, hydrochloride, followed by 1.67 ml. of triethylamine. The result is stirred overnight, and added to 300 ml. of water. The mixture is brought to pH 8.5 with saturated sodium bicarbonate, stirred with 100 ml. of ethyl acetate, and the yellow precipitate collected. It is chromatographed over 100 gm. of silica gel in a solvent mixture prepared from 500 parts acetonitrile, 250 parts water, 250 parts tetrahydrofuran, 1 part sodium acetate, and 0.1 part sodium bicarbonate, and the desired fractions are concentrated under reduced pressure. The yellow product, dihydrate, has UV absorption maxima at λ 380 (ε 25,200) and at 268 (ε 21,000), in 30% methanol-b 70% pH 7 buffer.

We claim:

1. A member of the class consisting of amido compounds of the formula

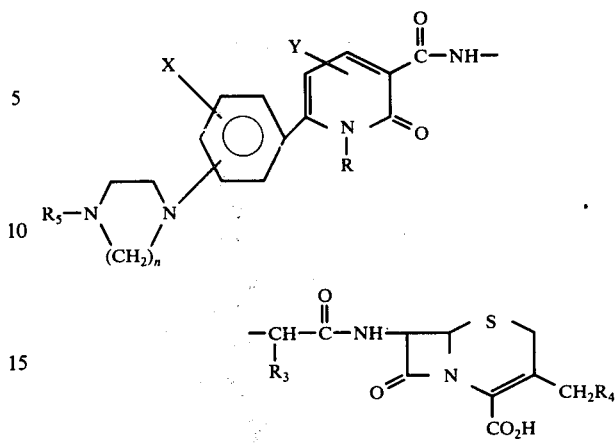

and pharmaceutically acceptable salts thereof; wherein R is hydrogen or methyl: $R_3$ is phenyl, p-hydroxyphenyl; 2-thienyl and cyclohexa-1,4-dien-1-yl, $R_4$ is hydrogen, acetoxy or 1-pyridyl with the proviso that when $R_4$ is 1-pyridyl, the $CO_2H$ is $—CO_2—$, and $R_5$ is a lower alkyl group of from one to six carbon atoms, cyclohexyl, benzyl, phenyl and halophenyl wherein halo represents chlorine, fluorine, bromine or iodo, X is hydrogen, chlorine or bromine; Y is hydrogen or bromine and $n$ is two or three with the proviso that when $n$ is three $R_5$ is methyl.

2. A compound according to claim 1 which is N-[6-[p-(4-methyl-1-piperazinyl)phenyl]-1,2-dihydro-2-oxonicotinyl]-cephaloglycin and pharmaceutically-acceptable salts thereof.

3. A compound according to claim 1 which is N-[6-[p-(4-methyl-1-piperazinyl)phenyl]-1,2-dihydro-2-oxonicotinyl]cephalexin and pharmaceutically-acceptable salts thereof.

4. A compound according to claim 1 which is 3-(1-pyridylmethyl)-7-[D-α-[6-[p-(4-methyl-1-piperazinyl)phenyl]-1,2-dihydro-2-oxonicotinamido]-α-phenylacetamido]-3-cephem-4-carboxylic acid betaine.

* * * * *